United States Patent [19]

Serrero

[11] Patent Number: 5,541,068
[45] Date of Patent: Jul. 30, 1996

[54] MAMMALIAN ADIPOCYTE PROTEIN P154, NUCLEIC ACIDS CODING THEREFOR AND USES THEREOF

[75] Inventor: Ginette Serrero, Lake Placid, N.Y.

[73] Assignee: W. Alton Jones Cell Science Center, inc., Lake Placid, N.Y.

[21] Appl. No.: 127,995

[22] Filed: Nov. 22, 1993

Related U.S. Application Data

[62] Division of Ser. No. 708,038, May 31, 1991, Pat. No. 5,268,295.

[51] Int. Cl.⁶ .......................... C07K 14/47; C07K 16/18; C07K 1/02; G01N 33/53
[52] U.S. Cl. .......................... 435/7.1; 435/29; 530/387.9; 530/388.1; 530/388.15; 530/388.2; 530/350; 436/63; 436/85; 436/86
[58] Field of Search ................................ 530/350, 387.9, 530/388.1, 388.15, 388.2; 435/7.1, 29; 436/63, 86, 85

Primary Examiner—Robert A. Wax
Assistant Examiner—Rebecca Prouty
Attorney, Agent, or Firm—Browdy and Neimark

[57] ABSTRACT

A mammalian adipocyte-specific polypeptide, termed p154, is expressed in high quantities in adipogenic cell lines after cell differentiation and is abundant in the fat pads of normal and genetically obese mammals. The murine and human polypeptide, DNA and RNA molecules coding therefor, methods for its preparation, and antibodies specific for the polypeptide are also disclosed. Methods for determining the susceptibility of a subject to obesity are based on measuring the levels of the adipocyte polypeptide in a biological fluid or tissue extract or by measuring mRNA encoding the polypeptide in cells of the subject. Methods of evaluating an anti-obesity drug comprise contacting the drug with an adipocyte in vitro and measuring the amount of the adipocyte polypeptide or mRNA produced by the adipocyte. Methods of treating a subject with obesity comprise administering the above antibody or blocking the expression of the p154 gene.

23 Claims, 9 Drawing Sheets

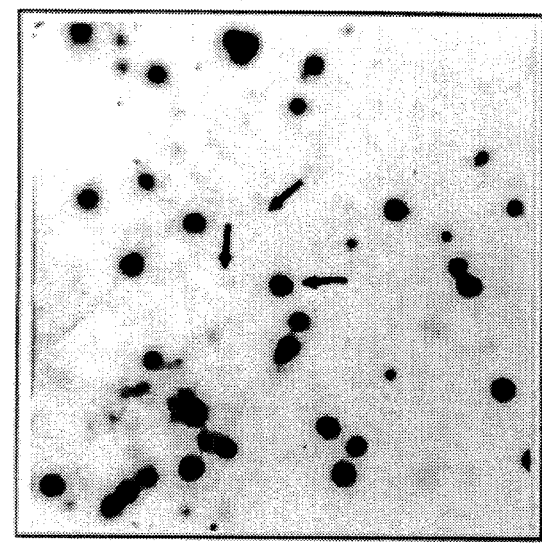
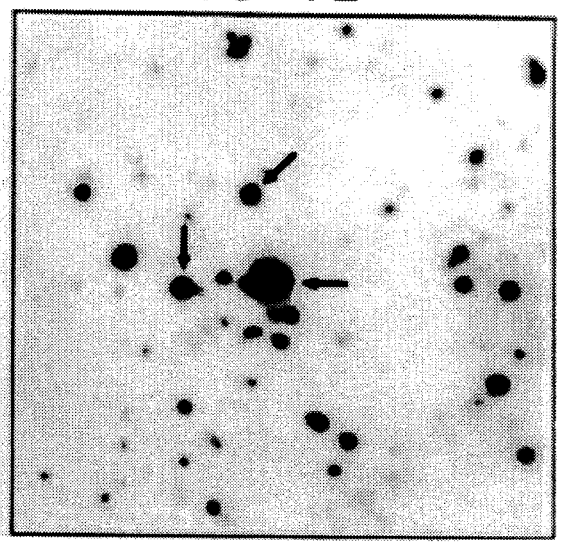
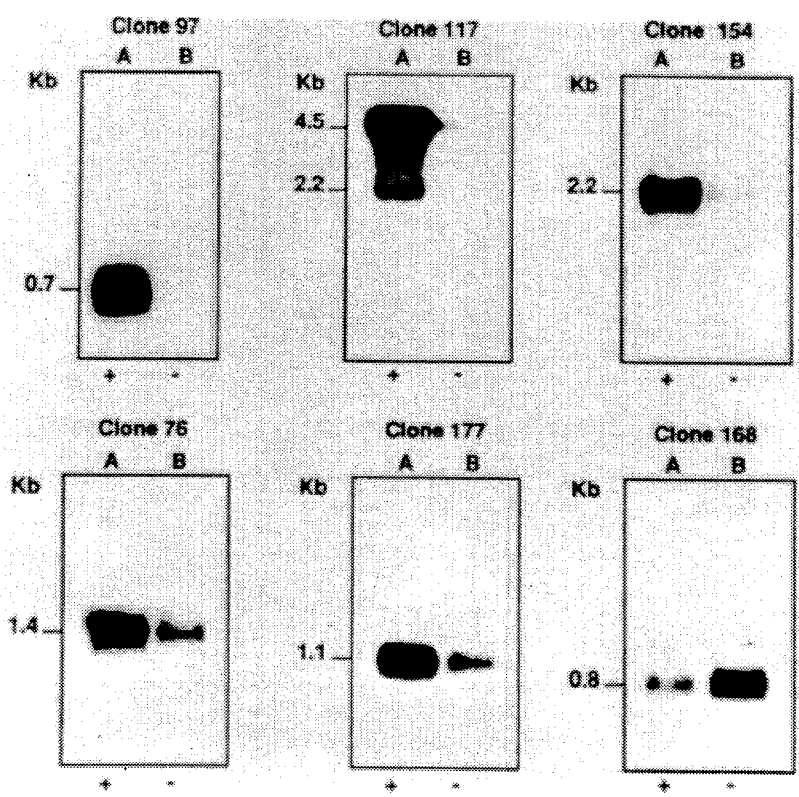

FIG. 10

HOMOLOGY BETWEEN MOUSE AND HUMAN p154 PROTEIN

```
MAAAVVDPQQSVVMRVANLPLVSSTYDLVSSAYVSTKDQYPYLRSVCEM-- AEKGVK T VT    58 mouse
                                                  :: ::: :: :
                                                  EFRAENGVK T I T   12 human SAAMTSALPI I QKLEPQI AVANTYACKGLDRMEERLPI LNQPTSE IVASAAGAVTGAK DV  118 mouse
:: :::::::::: ::::::::::::::::: :::::: ::::: ::::::::: :::
SVAMTSALPI I QKLEPQI AVANTYACKGLDR I EERLPI LNQPSTQIVANAKGAVTGAK DA   72 human VTTTMAGAKDSVASTVSGVVDKTKGAVTGSVERTKSVVNGSINTVLG-- M VQFMNSGVDN      176 mouse
:::  ::::::::: ::::::::::: :::::::::::::::::::  : :::  ::::
VTT VTGAKDSLAST ITGVMDKTKGAVTGSVEKTKSVVSGSINTVLGSR MMQL VSSGVEN   132 human AI TKSEMLVDQYFPLTQEELEMEAKKVEGFDMVQKPSNYERLESLSTKLC SRAYHQA LSR    236 mouse
:: :::: :::: :::
ALTKSE LLVDQYLPLT                                                  148 human VKEAKQKSQETISQLHSTVHL I EFARKNMHSANQKIQGAQDKLYVSWVEWKRSIGYDDTD      296 mouse ESHCVEH I ESRTLAIARNLTQQLQTTCQTVLVNAQGLPQ NIQDQAKHLGVMAGDIYS VFR   356 mouse NAASFKEVSDGVLTSSKGQLQKMKESLDEVMDYFVNNTPLNWLVGPFYPQS TEVNKASLK     416 mouse VQQSEVKAQZ                                                         426 mouse
```

[Aligned 146, Matches, 117, Mismatches, 31, Score 115, Homology 79%]

MAMMALIAN ADIPOCYTE PROTEIN P154, NUCLEIC ACIDS CODING THEREFOR AND USES THEREOF

This invention was funded in part by a research grant from the National Institutes of Health, No. DK38639, which provides to the United States Government certain rights in the invention.

This is a division of application Ser. No. 07/708,038 filed May 31, 1991, now U.S. Pat. No. 5,268,295.

BACKGROUND OF THE INVENTION

1. Field of the Invention

The invention in the field of cell biology, physiology and medicine relates to a purified mammalian adipocyte polypeptide, DNA encoding the polypeptide, antibodies thereto, and methods to determine susceptibility to obesity and for evaluating efficacy of anti-obesity drugs.

2. Description of the Background Art

Obesity has been declared a public health hazard by the National Institutes of Health. To combat this health problem, both prophylactic and therapeutic approaches are necessary. For prophylactic purposes, it would be useful to be able to predict and measure a person's propensity or susceptibility to obesity For therapeutic purposes, a means for interfering with the development of adipocytes (fat cells) would be of great benefit. Furthermore, as a broader preventative approach to obesity, the ability to limit the fat content of food mammals would be of great importance. None of these desired objectives has been achieved.

Early-onset obesity cannot be efficiently controlled by a weight reduction program once the obesity is apparent. Therefore, a means for early detection of early-onset obesity is imperative for its prevention.

Proteins that are unique to adipocytes would serve as prime targets for approaches directed to prediction and control of obesity. There have been no reports of proteins that are preferentially synthesized in fat pads of obese animals as compared to normal controls. In fact the opposite has been found, wherein adipsin mRNA and protein is decreased in fat pads and in the circulation of obese animals compared to normal littermates (Flier, J. S. et al., *Science* 237:405–408 (1987).

It is known that differentiation of mammalian adipogenic cells, precursors of fat cells, into fully differentiated adipocytes, is accompanied by the induction of particular proteins. For example, glycerol-3-phosphate dehydrogenase (G3PDH) and fatty acid binding protein have similar levels of mRNA expression in obese and nonobese animals (Flier et al., supra). Lipolytic and lipogenic enzymes, which are absent in the undifferentiated cells, are also induced during adipocyte differentiation. A gene for human lipoprotein lipase has been cloned and shown to be homologous in sequence to the mouse lipoprotein lipase sequence (Wion, K. L. et al., *Science* 235: 1038–1041 (1987); Kirchgessner, T. G. et al., *J. Biol. Chem.* 262.:8463–8466 (1987)). Structural similarity of the human to the rat lipoprotein lipase has also been disclosed (Holm, C. et al., *Biochim. Biophys. Acta* 1006:193–197 (1989)).

Several established cell lines which have the ability to undergo adipose differentiation in culture have been used as model systems to study adipose tissue development (Green, H. et al., *Cell* 1:113–116 (1974); Negrel, R. et al., *Proc. Natl. Acad. Sci. USA* 75:6054–6058 (1978); Hiragun, A. et al., *In Vitro* 16:685–693 (1980); Serrero, G. et al., *Anal. Biochem.* 120:351–359 (1982); Harrison, J. J. et al., *J. Cell Biol.* 100:429–434 (1985); Chapman, A. B., et al., *J. Biol. Chem.* 259:15548–15555 (1984); sparks, R. L. et al., *Cancer Res.* 46:5312–5319 (1986)). The differentiation of preadipocytes to adipocytes involve a series of events including morphological changes, induction of numerous proteins, alteration in hormonal receptors level and response (Green, H., In: *Obesity: Cellular and Molecular Aspects* (Ailhaud, A., ed.), Colloques de Inserm, pp 15–24 (1979); Coleman, R. A. et al., *J. Biol. Chem.* 253:7256–7261 (1978); Rubin, C. S. et al., *J. Biol. Chem.* 252:3554–3557 (1977); Reed, B. C. et al. Proc. Natl. Acad. Sci. USA 74:4876–4880 (1977); Rubin, C. S. et al., *J. Biol. Chem.* 253:7570–7578 (1978); Spiegelman, B. M. et al., *J. Biol. Chem.* 255:8811–8818 (1980)).

In the past several years, cDNA libraries of differentiated adipocytes have been constructed and screened either by differential hybridization (Chapman, A. B., et al., supra; Spiegelman, B. M. et al., *J. Biol. Chem.* 258:10083–10089 (1983); Bernlohr, D. A. et al., Proc. Natl. Acad. Sci. USA 81:5468–5472 (1984); Dani, C. et al., *Biol. Chem.* 264:10119–10125 (1989)) or by subtraction method (Smith, P. J. et al., *J. Biol. Chem.* 263:9402–9408 (1988)). The application of these techniques has led to the molecular characterization of cDNAs coding for proteins which are fat specific and which can play an important role in adipose tissue development.

The present inventor's laboratory has studied adipose differentiation using a C3H mouse teratoma-derived cell line called 1246 which has several interesting characteristics. The 1246 cell line is a bipotential cell line able to differentiate not only into adipocytes but also into muscle cells (Serrero, G., In: *Mammalian Cell Culture: The Use of Serum Free, Hormone Supplemented Media* (Mather, J. P., ed.), Plenum Press, New York pp. 53–75 (1984)). A defined medium supporting cell proliferation and differentiation has been described (Serrero, G., 1982, supra). In these conditions, the cells stringently require insulin for both processes. The differentiation of 1246 cells is stimulated by growth hormone and inhibited by tumor necrosis factor-α (TNFα), transforming growth factor-α (TGFβ), epidermal growth factor and transforming growth factor-α (Serrero, G., In: *Cellular Endocrinology: Hormonal Control of Embryonic and Cellular Differentiation* (Serrero, G. et al., eds.,) Alan R. Liss, Inc., New York, pp. 191–204 (1986)).

Several differentiation-deficient cell lines which display increased tumorigenic properties were isolated from 1246 cells maintained in the absence of insulin (Serrero, G. *In Vitro Cell. Devel. Biol.* 21:537–540 (1985)). These cells were shown to produce in their conditioned media several polypeptide growth factors which either stimulate their proliferation or modulate negatively their ability to differentiate (Yamada, Y. et al., *Proc. Natl. Acad. Sci. USA* 85:5936–5940 (1988); Yamada, Y. et al., *J. Cell. Physiol.* 140:354–263 (1989)). Thus 1246 and its differentiation-deficient counterparts are a useful model system for investigating the molecular mechanisms of gene expression during adipose differentiation.

SUMMARY OF THE INVENTION

The present inventor, using the 1246 cell line described above, constructed a ZAP cDNA library from fully differentiated 1246 cells. This library served as a source of probes for analyzing genes that are regulated during adipogenesis. Through the use of this library, the present inventor discovered and cloned cDNA molecules which encode mRNAs which are increased during adipose differentiation of 1246 cells. Furthermore, they have discovered a novel adipocyte-specific polypeptide encoded by this DNA and mRNA, termed "protein 154" or "p154." Furthermore, using the mouse cDNA, the inventor cloned and partially sequenced a human cDNA molecule encoding a human homologue of p154.

The murine p154 mRNA of the present invention has the following properties: (a) it is expressed in high quantities in adipogenic cell lines only after cell differentiation; (b) it is abundant in the fat pads of normal and genetically obese mice; and (c) its expression is 3- to 5-fold higher in the fat pads of Obese animals compared to the fat pads of their normal littermates.

The present invention is directed to a mammalian adipocyte polypeptide, p154, substantially free of other mammalian proteins, or a functional derivative thereof. The invention is also directed to a mammalian adipocyte polypeptide encoded by an mRNA molecule which is expressed in fat pad cells at a level of at least 10-fold higher than in brain, kidney or submaxillary gland cells, where the expression of the mRNA molecule is induced during differentiation of adipogenic cells. Preferably, the polypeptide is of human origin.

The present invention includes a polypeptide of at least about 10 amino acids encoded by at least a part of the DNA molecule which has the nucleotide sequence SEQ ID NO:1, or a functional derivative thereof. Preferably the polypeptide comprises the amino acid sequence extending from amino acids 1 through amino acid 425 of SEQ ID NO:2, or a functional derivative thereof.

In a preferred embodiment, the present invention is directed to a polypeptide of at least about 10 amino acids encoded by at least a part of the a DNA molecule which has the nucleotide sequence SEQ ID NO:3, or a functional derivative thereof. Preferably, the polypeptide comprises the amino acid sequence extending from amino acids 1 through amino acid 148 of SEQ ID NO:4, or a functional derivative thereof.

The present invention is also directed to a single or double stranded DNA molecule consisting essentially of a nucleotide sequence encoding the above polypeptide or encoding a functional derivative thereof, the DNA molecule being substantially free of other mammalian DNA sequences. The DNA molecule is preferably a single or double stranded DNA molecule having a nucleotide sequence consisting essentially of at least about 20 nucleotides of the nucleotide sequence SEQ ID NO:1 or a sequence complementary to at least part of SEQ ID NO:1, substantially free of other mammalian DNA sequences. In a preferred embodiment, the DNA molecule consists essentially of at least about 20 nucleotides of the nucleotide sequence SEQ ID NO:3 or a sequence complementary to at least part of SEQ ID NO:3, substantially free of other mammalian DNA sequences.

Included in the invention is a DNA molecule as described above which is cDNA or genomic DNA, preferably in the form of an expressible vehicle or plasmid.

The present invention is also directed to hosts transformed or transfected with the above DNA molecules, including a prokaryotic host, preferably a bacterium, a eukaryotic host such as a yeast cell or a mammalian cell.

In another aspect, the invention relates to an RNA molecule comprising a mRNA sequence encoding the above adipocyte polypeptide or a functionalderivative thereof.

The present invention also provides a process for preparing a mammalian adipocyte polypeptide, p154, or functional derivative as described above, the process comprising the steps of: (a) culturing a host capable of expressing the polypeptide under culturing conditions; (b) expressing the polypeptide; and (c) recovering the polypeptide from the culture.

Also included in the present invention is a method for detecting the presence of a nucleic acid molecule having the sequence of the DNA molecule described above in a nucleic acid-containing sample, the method comprising: (a) contacting the sample with an oligonucleotide probe complementary to the sequence under hybridizing conditions; and (b) measuring the hybridization of the probe to the nucleic acid molecule, thereby detecting the presence of the nucleic acid molecule. The above method may additionally comprise before step (a): (c) selectively amplifying the number of copies of the nucleic acid sequence.

Another embodiment of this invention is an antibody specific for an epitope of the adipocyte polypeptide p154 or functional derivative, either polyclonal or monoclonal.

Also intended is a method for detecting the presence or measuring the quantity of the adipocyte polypeptide p154 in a biological sample, comprising contacting the sample with the above antibody and detecting the binding of the antibody to an antigen in the sample, or measuring the quantity of antibody bound.

The present invention includes methods for determining the susceptibility of a subject to obesity which comprises removing a sample of a biological fluid or tissue from the subject and measuring therein the amount of the polypeptide p154 or mRNA coding therefor, where the amount of the polypeptide or mRNA is proportional to susceptibility.

Another method provided herein is for evaluating the efficacy of an anti-obesity drug which comprises contacting the drug being tested with an adipocyte in vitro and measuring the amount of the polypeptide p154 or mRNA is produced by the adipocyte, the efficacy of the drug being proportional to the decrease in the production of the polypeptide or mRNA.

BRIEF DESCRIPTION OF THE DRAWINGS

FIG. 1A and B show the screening of the cDNA library for differentiation-related genes in 1246 cells. Duplicate sets of nitrocellulose filters containing phage plaques of cDNA library of differentiated 1246 cells were hybridized with equivalent amounts of $^{32}$P-labeled cDNA synthesized from poly(A+)-RNA of 1246-preadipocytes (A) or 1246-adipocytes (B). Arrows indicate two plaques which yield much stronger signals when hybridized to adipocyte cDNA than to preadipocyte cDNA.

FIG. 2 shows a northern analysis of the expression of several cDNA clones before and after adipogenesis of 1246 cells. Total RNA isolated from fully differentiated 1246 cells (A) and 1246 preadipocytes (B) was loaded on each lane.

FIG. 10 shows the homology between amino acid sequences of p154 mouse (SEQ ID NO:2) and human (SEQ ID NO:4).

DETAILED DESCRIPTION OF PREFERRED EMBODIMENTS

Figure 3:
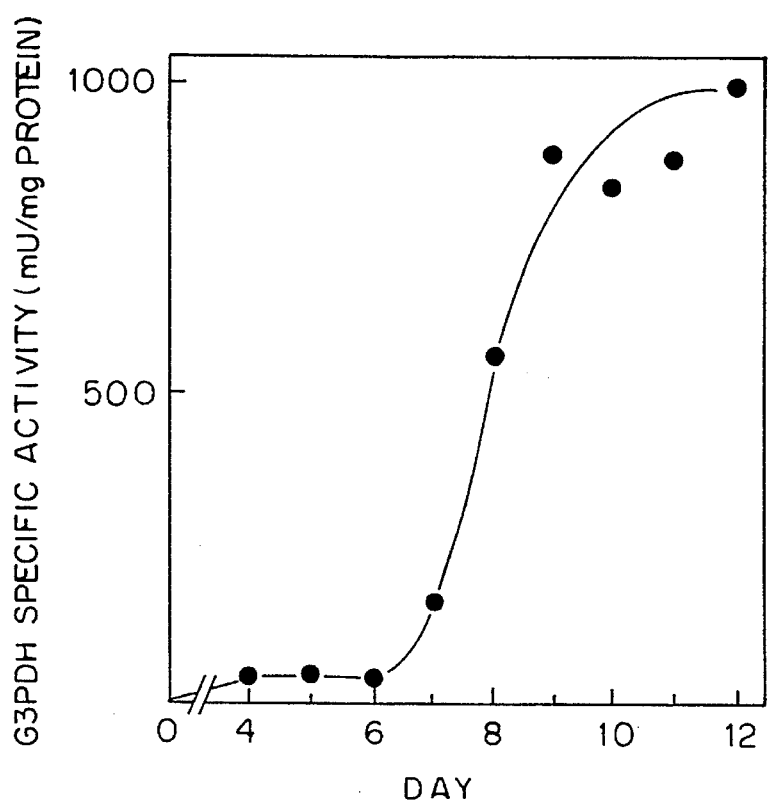
FIG. 3 is a graph showing the increase in G3PDH specific activity during adipogenesis of 1246 cells. When the cells reached confluence (day 4 of culture) they were treated with DEX-MIX-INDO for 48 hrs. Results depict enzymatic activity assay from day 4 to day 13 of culture.

The present invention is directed to RNA and DNA molecules encoding human or murine p154 and their homologues in other mammals, as well as the human or murine p154 protein and homologues in other mammals. These molecules are useful as targets of anti-obesity therapy. Such therapy can be achieved by the use of antisense methodology, wherein expression of p154 is inhibited, or by treatment with an antibody specific for p154. The p154 protein and functional derivatives thereof and antibodies specific for these molecules are used in assays that can predict obesity and can be utilized for the development of commercially valuable anti-obesity drugs.

In its first aspect, the present invention provides a mammalian adipocyte polypeptide, termed p154, preferably human p154, that is encoded by a mRNA molecule which, in young and non-senescent adult mammals, is preferentially expressed in fat pad cells as compared to brain, kidney or submaxillary gland cells.

The p154-encoding mRNA molecule is induced during differentiation of adipogenic cells into adipocytes. "Primary culture adipocyte precursor cells" are cultures started from fresh explants of adipocyte precursor cells.

By the term "preferentially expressed" means an amount of mRNA or protein per cell of the fat pad that is at least 10 times that per cell of brain, kidney or submaxillary gland.

The term "polypeptide" as used herein is intended to include not only p154 and functional derivatives thereof (see below), but also amino acid sequences having additional components such as a sugar, as in a glycoprotein or glycopeptide, or other modified protein structures known in the art.

The polypeptide of the invention has an amino acid sequence according to SEQ ID NO:2, or preferably, an amino acid sequence according to SEQ ID NO:4. Also intended within the scope of the present invention is any peptide having at least about 10 amino acids present in the above-mentioned sequences. Sequences of this length are useful as antigens and for making immunogenic conjugates with carriers for the production of antibodies specific for various epitopes of the entire protein. Such peptides are also useful in screening such antibodies and in the methods of the present invention directed to detection of the p154 protein in biological samples. It is well-known in the art that peptides of about 10 amino acids are useful in generation of antibodies to larger proteins of biological interest, e.g., TGFα (Nestor, J. J. et al., *Biochem. Biophys. Res. Comm.* 129:226–232 (1985)).

The polypeptide of this invention may exist covalently or noncovalently bound to another molecule. For example it may be fused to one or more other polypeptides via one or more peptide bonds. In one embodiment, the p154 molecule is fused to glutathione transferase protein.

The polypeptide is sufficiently large to comprise an antigenically distinct determinant or epitope, which can be used as an immunogen, to produce antibodies against p154 or a functional derivative thereof (see below), and to test such antibodies.

One embodiment includes the polypeptide substantially free of other mammalian peptides. The polypeptide of the present invention may be biochemically or immunochemically purified from cells, tissues or a biological fluid. Alternatively, the polypeptide can be produced by recombinant means in a prokaryotic or eukaryotic host cell.

"Substantially free of other mammalian polypeptides" reflects the fact that, because the gene for the adipocyte polypeptide of interest here can be synthesized, the polypeptide can be synthesized in a prokaryotic organism or non-mammalian eukaryotic organism, if desired. Alternatively, methods are well known for the synthesis of polypeptides of desired sequence on solid phase supports and their subsequent separation from the support. Alternatively, the protein can be purified from tissue or fluids of the mammal in which it naturally occurs so that it is purified away from at least 90 per cent (on a weight basis), and from even at least 99 per cent if desired, of other mammalian polypeptides and is therefore substantially free of them. That can be achieved by subjecting the tissue or fluids to standard protein purification techniques such as immunoadsorbent columns bearing monoclonal antibodies reactive against the protein. Alternatively, the purification from such tissue or fluids can be achieved by a combination of standard methods, such as ammonium sulfate precipitation, molecular sieve chromatography, and ion exchange chromatography. As alternatives to a native purified or recombinant mammalian adipocyte polypeptide molecule, functional derivatives of the mammalian adipocyte polypeptide may be used.

By "functional derivative" is meant a "fragment," "variant," "analog," or "chemical derivative" of the mammalian adipocyte polypeptide, which terms are defined below. A functional derivative retains at least a portion of the function of the mammalian adipocyte polypeptide which permits its utility in accordance with the present invention.

A "fragment" of the mammalian adipocyte polypeptide refers to any subset of the molecule, that is, a shorter peptide.

A "variant" of the mammalian adipocyte polypeptide refers to a molecule substantially similar to either the entire peptide or a fragment thereof. Variant peptides may be conveniently prepared by direct chemical synthesis of the variant peptide, using methods well-known in the art.

Alternatively, amino acid sequence variants of the peptide can be prepared by mutations in the DNA which encodes the synthesized peptide. Such variants include, for example, deletions from, or insertions or substitutions of, residues within the amino acid sequence. Any combination of deletion, insertion, and substitution may also be made to arrive at the final construct, provided that the final construct possesses the desired activity. Obviously, the mutations that will be made in the DNA encoding the variant peptide must not alter the reading frame and preferably will not create complementary regions that could produce secondary mRNA structure (see European Patent Publication No. EP 75,444).

At the genetic level, these variants ordinarily are prepared by site-directed mutagenesis of nucleotides in the DNA encoding the peptide molecule, thereby producing DNA encoding the variant, and thereafter expressing the DNA in recombinant cell culture. The variants typically exhibit the same qualitative biological activity as the nonvariant peptide.

Preparation of a peptide variant in accordance herewith is preferably achieved by site-specific mutagenesis of DNA that encodes an earlier prepared variant or a nonvariant version of the p154 protein or a peptide thereof. Site-specific mutagenesis allows the production of peptide variants through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. The technique of site-specific mutagenesis is well known in the art, as exemplified by Adelman et al., *DNA* 2:183 (1983). Typical vectors useful in site-directed mutagenesis include vectors such as the M13 phage, for example, as disclosed by Messing et al., *Third Cleveland Symposium on Macromolecules and Recombinant DNA*, Walton, A., ed., Elsevier, Amsterdam (1981). These phage are readily commercially available and their use is generally well known to those skilled in the art. Alternatively, plasmid vectors that contain a single-stranded phage origin of replication (Veira et al., *Meth. Enzymol.* 153:3 (1987)) may be employed to obtain single-stranded DNA.

In general, site-directed mutagenesis in accordance herewith is performed by first obtaining a single-stranded vector that includes within its sequence a DNA sequence that encodes the relevant peptide. An oligonucleotide primer bearing the desired mutated sequence is prepared, generally synthetically, for example, by the method of Crea et al., *Proc. Natl. Acad. Sci. (USA)* 75:5765 (1978). This primer is then annealed with the single-stranded protein-sequence-containing vector, and subjected to DNA-polymerizing enzymes such as *E. coli* polymerase I Klenow fragment, to complete the synthesis of the mutation-bearing strand. Thus, a mutated sequence and the second strand bears the desired mutation. This heteroduplex vector is then used to transform appropriate cells and clones are selected that include recombinant vectors bearing the mutated sequence arrangement. The mutated protein region may be removed and placed in an appropriate vector for protein production, generally an expression vector of the type that may be employed for transformation of an appropriate host.

An example of a terminal insertion includes a fusion of a signal sequence, whether heterologous or homologous to the host cell, to the N-terminus of the peptide molecule to facilitate the secretion of mature peptide molecule from recombinant hosts. Another group of variants are those in which at least one amino acid residue in the peptide molecule, and preferably, only one, has been removed and a different residue inserted in its place. For a detailed description of protein chemistry and structure, see Schulz, G. E. et al., *Principles of Protein Structure*, Springer-Verlag, New York, 1978, and Creighton, T. E., *Proteins: Structure and Molecular Properties*, W. H. Freeman & Co., San Francisco, 1983, which are hereby incorporated by reference. The types of substitutions which may be made in the protein or peptide molecule of the present invention may be based on analysis of the frequencies of amino acid changes between a homologous protein of different species, such as those presented in Table 1–2 or Schulz et al. (supra) and FIG. 3–9 of Creighton (supra). Base on such an analysis, conservative substitutions are defined herein as exchanges within one of the following five groups:

1. Small aliphatic, nonpolar or slightly polar residues: ala, ser, thr (pro, gly);
2. Polar, negatively charged residues and their amides: asp, asn, glu, gln;
3. Polar, positively charged residues: his, arg, lys;
4. Large aliphatic, nonpolar residues: met, leu, ile, val (cys); and
5. Large aromatic residues: phe, tyr, trp.

The three amino acid residues in parentheses above have special roles in protein architecture. Gly is the only residue lacking any side chain and thus imparts flexibility to the chain. Pro, because of its unusual geometry, tightly constrains the chain. Cys can participate in disulfide bond formation which is important in protein folding. Note the Schulz et al. would merge Groups 1 and 2, above. Note also that Tyr, because of its hydrogen bonding potential, has some kinship with Ser, Thr, etc.

Substantial changes in functional or immunological properties are made by selecting substitutions that are less conservative, such as between, rather than within, the above five groups, which will differ more significantly in their effect on maintaining (a) the structure of the peptide backbone in the area of the substitution, for example, as a sheet or helical conformation, (b) the charge or hydrophobicity of the molecule at the target site, or (c) the bulk of the side chain. Examples of such substitutions are (a) substitution of gly and/or pro by another amino acid or deletion or insertion of gly or pro; (b) substitution of a hydrophilic residue, e.g., ser or thr, for (or by) a hydrophobic residue, e.g., leu, ile, phe, val or ala; (c) substitution of a cys residue for (or by) any other residue; (d) substitution of a residue having an electropositive side chain, e.g., lys, arg or his, for (or by) a residue having an electronegative charge, e.g., glu or asp; or (e) substitution of a residue having a bulky side chain, e.g., phe, for (or by) a residue not having such a side chain, e.g., gly.

Most deletions and insertions, and substitutions according to the present invention are those which do not produce radical changes in the characteristics of the protein or peptide molecule. However, when it is difficult to predict the exact effect of the substitution, deletion, or insertion in advance of doing so, one skilled in the art will appreciate that the effect will be evaluated by routine screening assays. For example, a variant typically is made by site-specific mutagenesis of the peptide molecule-encoding nucleic acid, expression of the variant nucleic acid in recombinant cell culture, and, optionally, purification from the cell culture, for example, by immunoaffinity chromatography using a specific antibody on a column (to absorb the variant by binding to at least one epitope).

The activity of the cell lysate or purified protein or peptide variant can be screened in a suitable screening assay for the desired characteristic. For example, a change in the immunological character of the protein peptide molecule, such as binding to a given antibody, is measured by a competitive type immunoassay (see below). Biological activity is screened in an appropriate bioassay, as described below.

Modifications of such peptide properties as redox or thermal stability, hydrophobicity, susceptibility to proteolytic degradation or the tendency to aggregate with carriers or into multimers are assayed by methods well known to the ordinarily skilled artisan.

An "analog" of the mammalian adipocyte polypeptide refers to a non-natural molecule substantially similar to either the entire molecule or a fragment thereof.

A "chemical derivative" of the mammalian adipocyte polypeptide or peptide contains additional chemical moieties not normally a part of the polypeptide. Covalent modifications are included within the scope of this invention. Such modifications may be introduced into the molecule by reacting targeted amino acid residues with an organic derivatizing agent that is capable of reacting with selected side chains or terminal residues.

Cysteinyl residues most commonly are reacted with alpha-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, alpha-bromo-beta-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5–7.0 because this agent is relatively specific for the histidyl side chain. Parabromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing alpha-amino-containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues per se has been studied extensively, with particular interest in introducing spectral labels into tyrosyl residues by reaction with aromatic diazonium compounds or tetranitromethane. Most commonly, N-acetylimidizol and tetranitromethane are used to form O-acetyl tyrosyl species and 3-nitro derivatives, respectively.

Carboxyl side groups (aspartyl or glutamyl) are selectively modified by reaction with carbodiimides (R'-N-C-N-R') such as 1-cyclohexyl-3-(2-morpholinyl-(4-ethyl) carbodiimide or 1-ethyl-3 (4 azonia 4,4-dimethylpentyl) carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

Derivatization with bifunctional agents is useful for cross-linking the peptide to a water-insoluble support matrix or to other macromolecular carriers. Commonly used cross-linking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(pazidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Other modifications include hydroxylation of proline and lysine, phosphorylation of hydroxyl groups of seryl or threonyl residues, methylation of the alpha-amino groups of lysine, arginine, and histidine side chains (T. E. Creighton, *Proteins: Structure and Molecule Properties*, W. H. Freeman & Co., San Francisco, pp. 79–86 (1983)), acetylation of the N-terminal amine, and, in some instances, amidation of the C-terminal carboxyl groups.

Such derivatized moieties may improve the solubility, absorption, biological half life, and the like. The moieties may alternatively eliminate or attenuate any undesirable side effect of the protein and the like. Moieties capable of mediating such effects are disclosed, for example, in *Remington's Pharmaceutical Science*. 16th ed., Mack Publishing Co., Easton, Pa. (1980)

The polypeptide of the present invention is encoded by a nucleotide sequence one strand of which has the nucleotide sequence SEQ ID NO:1 or preferably, SEQ ID NO:3. The present invention is directed to a DNA sequence encoding the p154 polypeptide or a functional derivative thereof, substantially free of other mammalian DNA sequences. Such DNA may be single or double stranded.

The DNA sequence should preferably have about 20 or more nucleotides to allow hybridization to another polynucleotide. In order to achieve higher specificity of hybridization, characterized by the absence of hybridization to sequences other than those encoding the p154 protein or a homologue or functional derivative thereof, a length of at least about 50 nucleotides is preferred.

The present invention is also directed to an RNA molecule comprising a mRNA sequence encoding the p154 polypeptide molecule of the invention or a functional derivative thereof.

The present invention is further directed to the above DNA molecules which are expressible vehicles or vectors, as well as hosts transfected or transformed with the vehicles and capable of expressing the polypeptide. Such hosts may be prokaryotic, preferably bacteria, or eukaryotic, preferably yeast or mammalian cells. The DNA can be incorporated into the host organism by transformation, transduction, transfection, or a related process known in the art.

In addition to a DNA and mRNA sequence encoding a adipocyte polypeptide molecule, the invention provides methods for expression of these nucleic acid sequences. Further, the genetic sequences and oligonucleotides of the invention allow the identification and cloning of additional, yet undiscovered adipocyte polypeptides having sequence homology to the adipocyte polypeptide described herein.

The recombinant DNA molecules of the present invention can be produced through any of a variety of means, such as, for example, DNA or RNA synthesis, or more preferably., by application of recombinant DNA techniques. Techniques for synthesizing such molecules are disclosed by, for example, Wu, R., et al. (*Prog. Nucl. Acid. Res. Molec. Biol.* 21:101–141 (1978)). Procedures for constructing recombinant molecules in accordance with the above-described method are disclosed by Sambrook et al., *Molecular Cloning: A Laboratory Manual*, Second Edition, Cold Spring Harbor Press, Cold Spring Harbor, N.Y. (1989), which reference is herein incorporated by reference.

The 3' terminus of the recombinant molecule of this invention is preferably treated to render it unsuitable for polymerization. Such treatment may be accomplished by blocking the terminus by chemical means, or by modifying the terminal bases such that they sterically interfere with polymerase action. In a preferred embodiment, such treatment is accomplished by immobilizing the 3' terminus, such as by coupling it to a solid support (such as, for example, glass, plastic, latex, etc.). The support maybe of any form (i.e. a sheet, rod, sphere, ovoid, etc. Procedures for such immobilization are well known to those of ordinary skill. In the most preferred embodiment, the 3' end of the recombinant molecule is covalently bound to the solid support. A spacer region may be used to extend the probe outward from the solid support as long as (1) it will not sterically hinder any function or characteristic of the recombinant molecule, and (2) the sequence of the spacer region does not participate in the hybridization or polymerization reactions of the assay. It is typically desirable to immobilize several, and preferably, a large number of Such recombinant molecule to the support.

Oligonucleotides representing a portion of an adipocyte polypeptide are useful for screening for the presence of genes encoding such proteins and for the cloning of adipocyte polypeptide genes. Techniques for synthesizing such oligonucleotides are disclosed by, for example, Wu, R., et al., *Prog. Nucl. Acid. Res. Molec. Biol.* 21:101–141 (1978)).

Protein molecules are fragmented as with cyanogen bromide, or with proteases such as papain, chymotrypsin, trypsin, etc. (Oike, Y., et al., *J. Biol. Chem.* 257:9751–9758 (1982); Liu, C., et al., *Int. J. Pept. Protein Res.* 21:209–215 (1983)). Because the genetic code is degenerate, more than one codon may be used to encode a particular amino acid (Watson, J. D., In: Molecular Biology of the Gene, 4th Ed., Benjamin/Cummings Publishing Co., Inc., Menlo Park, Calif. (1987)). Using the genetic code, one or more different oligonucleotides can be identified, each of which would be capable of encoding the amino acid. The probability that a particular oligonucleotide will, in fact, constitute the actual XXX-encoding sequence can be estimated by considering abnormal base pairing relationships and the frequency with which a particular codon is actually used (to encode a particular amino acid) in eukaryotic cells. Such "codon usage rules" are disclosed by Lathe, R., et al., *J. Molec. Biol.* 183:1–12 (1985). Using the "codon usage rules" of Lathe, a single oligonucleotide, or a set of oligonucleotides, that contains a theoretical "most probable" nucleotide sequence capable of encoding the adipocyte polypeptide sequences is identified.

Although occasionally an amino acid sequences may be encoded by only a single oligonucleotide, frequently the amino acid sequence may be encoded by any of a set of similar oligonucleotides. Importantly, whereas all of the members of this set contain oligonucleotides Which are capable of encoding the peptide fragment and, thus, potentially contain the same oligonucleotide sequence as the gene which encodes the peptide fragment, only one member of the set contains the nucleotide sequence that is identical to the nucleotide sequence of the gene. Because this member is present within the set, and is capable of hybridizing to DNA even in the presence of the other members of the set, it is possible to employ the unfractionated set of oligonucleotides in the same manner in which one would employ a single oligonucleotide to clone the gene that encodes the peptide.

The oligonucleotide, or set of oligonucleotides, containing the theoretical "most probable" sequence capable of encoding the adipocyte polypeptide fragment is used to identify the sequence of a complementary oligonucleotide or set of oligonucleotides which is capable of hybridizing to the "most probable" sequence, or set of sequences. An oligonucleotide containing such a complementary sequence can be employed as a probe to identify and isolate the adipocyte polypeptide gene (Sambrook et al., supra). A nucleic acid probe, preferably an oligonucleotide, typically has a detectable label, such as a radiolabel, a. light-absorbing or light emitting label, or the like.

A suitable oligonucleotide, or set of oligonucleotides, polypeptide gene (or which is complementary to such an oligonucleotide, or set of oligonucleotides) is identified (using the above-described procedure), synthesized, and hybridized by means well known in the art, against a DNA or, more preferably, a cDNA preparation derived from cells which are capable of expressing the adipocyte polypeptide gene. Single stranded oligonucleotide molecules complementary to the "most probable" adipocyte polypeptide-encoding sequences can be synthesized using procedures which are well known to those of ordinary skill in the art (Belagaje, R., et al., *J. Biol. Chem.* 254:5765–5780 (1979); Maniatis, T., et al., *Molecular Mechanisms in the Control of Gene Expression*, Nierlich, D. P., et al., Eds., Acad. Press, NY (1976); Wu, R., et al., *Prog. Nucl. Acid Res. Molec. Biol.* 21:101–141 (1978); Khorana, R. G., *Science* 203:614–625 (1979)). Additionally, DNA synthesis may be achieved through the use of automated synthesizers. Techniques of nucleic acid hybridization are disclosed by Sambrook et al. (supra), and by Haymes, B. D., et al. (In: *Nucleic Acid Hybridization, A Practical Approach*, IRL Press, Washington, D.C. (1985)), which references are herein incorporated by reference. Techniques such as, or similar to, those described above have successfully enabled the cloning of genes for human aldehyde dehydrogenases (Hsu, L. C., et al., *Proc. Natl. Acad. Sci. USA* 82:3771–3775 (1985)), fibronectin (Suzuki, S., et al., *Eur. Mol. Biol. Organ. J.* 4:2519–2524 (1985)), the human estrogen receptor gene (Walter, P., et al., *Proc. Natl. Acad. Sci. USA* 82: 7889–7893 (1985)), tissue-type plasminogen activator (Pennica, D., et al., *Nature* 301:214–221 (1983)) and human term placental alkaline phosphatase complementary DNA (Kam, W., et al., *Proc. Natl. Acad. Sci. USA* 82:8715–8719 (1985)).

In a alternative way of cloning the adipocyte polypeptide gene, a library of expression vectors is prepared by cloning DNA or, more preferably, cDNA (from a cell capable of expressing adipocyte polypeptide) into an expression vector. The library is then screened for members capable of expressing a protein which binds to anti-adipocyte polypeptide antibody, and which has a nucleotide sequence that is capable of encoding polypeptides that have the same amino acid sequence as adipocyte polypeptide, or fragments thereof. In this embodiment, DNA, or more preferably cDNA, is extracted and purified from a cell which is capable of expressing adipocyte polypeptide protein. The purified cDNA is fragmentized (by shearing, endonuclease digestion, etc.) to produce a pool of DNA or cDNA fragments. DNA or cDNA fragments from this pool are then cloned into an expression vector in order to produce a genomic library of expression vectors whose members each contain a unique cloned DNA or cDNA fragment.

An "expression vector" is a vector which (due to the presence of appropriate transcriptional and/or translational control sequences) is capable of expressing a DNA (or cDNA) molecule which has been cloned into the vector and of thereby producing a polypeptide or protein. Expression of the cloned sequences occurs when the expression vector is introduced into an appropriate host cell. If a prokaryotic expression vector is employed, then the appropriate host cell would be any prokaryotic cell capable of expressing the cloned sequences. Similarly, if a eukaryotic expression vector is employed, then the appropriate host cell would be any eukaryotic cell capable of expressing the cloned sequences. Importantly, since eukaryotic DNA may contain intervening sequences, and since such sequences cannot be correctly processed in prokaryotic cells, it is preferable to employ cDNA from a cell which is capable of expressing adipocyte polypeptide in order to produce a prokaryotic genomic expression vector library. Procedures for preparing cDNA and for producing a genomic library are disclosed by Sambrook et al. (supra).

A DNA sequence encoding the adipocyte polypeptide of the present invention, or its functional derivatives, may be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed by Sambrook et al., supra, and are well known in the art.

A nucleic acid molecule, such as DNA, is said to be "capable of expressing" a polypeptide if it contains nucleotide sequences which contain transcriptional and translational regulatory information and such sequence are "operably linked" to nucleotide sequences which encode the polypeptide. An operable linkage is a linkage in which the regulatory DNA sequences and the DNA sequence sought to be expressed are connected in such a way as to permit gene expression. The precise nature of the regulatory regions needed for gene expression may vary from organism to organism, but shall in general include a promoter region which, in prokaryotes, contains both the promoter (which directs the initiation of RNA transcription) as well as the DNA sequences which, when transcribed into RNA, will signal the initiation of protein synthesis. Such regions will normally include those 5'-non-coding sequences involved with initiation of transcription and translation, such as the TATA box, capping sequence, CAAT sequence, and the like.

If desired, the non-coding region 3' to the gene sequence coding for the protein may be obtained by the above-described methods. This region may be retained for its transcriptional termination regulatory sequences, such as termination and polyadenylation. Thus, by retaining the 3-' region naturally contiguous to the DNA sequence coding for the protein, the transcriptional termination signals may be provided. Where the transcriptional termination signals are not satisfactorily functional in the expression host cell, then a 3' region functional in the host cell may be substituted.

Two DNA sequences (such as a promoter region sequence and a adipocyte polypeptide-encoding sequence) are said to be operably linked if the nature of the linkage between the two DNA sequences does not (1) result in the introduction of a frame-shift mutation, (2) interfere with the ability of the promoter region sequence to direct the transcription of the adipocyte polypeptide gene sequence, or (3) interfere with the ability of the adipocyte polypeptide gene sequence to be transcribed by the promoter region sequence. A promoter region would be operably linked to a DNA sequence if the promoter were capable of effecting transcription of that DNA sequence. Thus, to express the protein, transcriptional and translational signals recognized by an appropriate host are necessary.

A promoter is a double-stranded DNA or RNA molecule which is capable of binding RNA polymerase and promoting the transcription of an "operably linked" nucleic acid sequence. As used herein, a "promoter sequence" is the sequence of the promoter which is found on that strand of the DNA or RNA which is transcribed by the RNA polymerase. A "promoter sequence complement" is a nucleic acid molecule whose sequence is the complement of a "promoter sequence." Hence, upon extension of a primer DNA or RNA adjacent to a single-stranded "promoter sequence complement" or, of a "promoter sequence," a double-stranded molecule is created which will contain a functional promoter, if that extension proceeds towards the "promoter sequence" or the "promoter sequence complement." This functional promoter will direct the transcription of a nucleic acid molecule which is operably linked to that strand of the double-stranded molecule which contains the "promoter sequence" (and not that strand of the molecule which contains the "promoter sequence complement").

Certain RNA polymerases exhibit a high specificity for such promoters. The RNA polymerases of the bacteriophages T7, T3, and SP-6 are especially well characterized, and exhibit high promoter specificity. The promoter sequences which are specific for each of these RNA polymerases also direct the polymerase to utilize (i.e. transcribe) only one strand of the two strands of a duplex DNA template. The.selection of which strand is transcribed is determined by the orientation of the promoter sequence. This selection determines the direction of transcription since RNA is only polymerized enzymatically by the addition of a nucleotide 5' phosphate to a 3' hydroxyl terminus.

Two sequences of a nucleic acid molecule are said to be "operably linked" when they are linked to each other in a manner which either permits both sequences to be transcribed onto the same RNA transcript, or permits an RNA transcript, begun in one sequence to be extended into the second sequence. Thus, two sequences, such as a promoter sequence and any other "second" sequence of DNA or RNA are operably linked if transcription commencing in the promoter sequence will produce an RNA transcript of the operably linked second sequence. In order to be "operably linked" it is not necessary that two sequences be immediately adjacent to one another.

Thus, as indicated above, in order to function as a promoter, a promoter sequence must be present as a double-stranded molecule. For the purposes of the present invention, the two strands of a functional promoter sequence are referred to as a "transcript" strand and a "complementary" strand. The "transcript" strand is that strand of the duplex which will be transcribed by the RNA polymerase (i.e. which serves as the template for transcription). The "complementary" strand is the strand which has a sequence complementary to the "transcript" strand, and which must be present, and hybridized to the "transcript" strand, in order for transcription to occur. Thus, when the "transcript" strand of a promoter sequence is operably linked to a second sequence, hybridization of the "transcript" strand with the "complement" strand, will, in the presence of a polymerase, result in the transcription of the "transcript" strand, and will produce an RNA transcript using the sequence of the "transcript" strand as a template.

The promoter sequences of the present invention may be either prokaryotic, eukaryotic or viral. Suitable promoters are repressible, or, more preferably, constitutive. Examples of suitable prokaryotic promoters include promoters capable of recognizing the T4 polymerase (Malik, S. et al., *J. Biol. Chem.* 263:1174–1181 (1984); Rosenberg, A. H. et al., *Gene* 59:191–200 (1987); Shinedling, S. et al., *J. Molec. Biol.* 195:471–480 (1987)), the T3, Sp6, or T7 polymerases (Chamberlin, M. et al., *Nature* 228:227–231 (1970); Bailey, J. N. et al., *Proc. Natl. Acad. Sci. (U.S.A.).* 80:2814–2818(1983); Davanloo, P. et al., *Proc. Natl. Acad. Sci. (U.S.A.)* 81:2035–2039 (1984)). Other suitable promoters are the PR and PL promoters of bacteriophage lambda (*The Bacteriophage Lambda*, Hershey, A. D., Ed., Cold Spring Harbor Press, Cold Spring Harbor, N.Y. (1973); Lambda II, Hendrix, R. W., Ed., Cold Spring Harbor Press, Cold Spring Harbor, N.Y. (1980)); the trp, recA, heat shock, and lacZ promoters of *E. coli*; the α-amylase (Ulmanen, I., et al., *J. Bacteriol.* 162:176–182 (1985)) and the σ-28-specific promoters of *B. subtilis* (Gilman, M. Z., et al., *Gene* 32:11–20 (1984)); the promoters of the bacteriophages of *Bacillus* (Gryczan, T. J., In: *The Molecular Biology of the Bacilli*, Academic Press, Inc., NY (1982)); *Streptomyces* promoters (Ward, J. M., *Mol. Gen. Genet.* 203:468–478 (1986)); the int promoter of bacteriophage lambda; the bla promoter of the β-lactamase gene of pBR322, and the CAT promoter of the chloramphenicol acetyl transferase gene of pPR325, etc. Prokaryotic promoters are reviewed by Glick, B. R., (*J. Ind. Microbiol.* 1:277–282 (1987)); Cenatiempo, Y. (*Biochimie* 68:505–516 Watson, J. D. et al. (In: *Molecular Biology of the Gene*, Fourth Edition, Benjamin Cummins, Menlo Park, Calif. (1987)); and Gottesman, S. (*Ann. Rev. Genet.* 18:415–442 (1984)).

Preferred eukaryotic promoters include the promoter of the mouse metallothionein I gene (Hamer, D., et al., *J. Mol. Appl. Gen.* 273–288 (1982)); the TK promoter of Herpes virus (McKnight, S., *Cell* 31:355–365 (1982)); the SV40 early promoter (Benoist, C., et al., *Nature* (London) 290:304–310 (1981)); and the yeast gal.4 gene promoter (Johnston, S. A., et al., *Proc. Natl. Acad. Sci. (USA)* 79:6971–6975 (1982); Silver, P. A., et al., *Proc. Natl. Acad. Sci. (USA)* 5951–5955 (1984)). All of the above listed references are incorporated by reference herein.

Strong promoters are preferred. Examples of such preferred promoters are those which recognize the T3, SP6 and T7 polymerases, the $P_L$ promoter of bacteriophage lambda, the recA promoter, the promoter of the mouse metallothionein I gene, and an SV40 promoter, such as that driving transcription in the pLSV vector (Livneh, E., et al., (1986) *J. Biol. Chem.* 261, 12490–12497).

The constitutive expression of antisense RNA in cells has been shown to inhibit the expression of about 20 different genes in mammals and plants, and the list continually grows (Hambor, J. E. et al., *J. Exp. Med.* 168:1237–1245 (1988); Holt, J. T. et al., *Proc. Natl. Acad. Sci. USA* 83:4794–4798 (1986); Izant, J. G. et al., *Cell* 36:1007–1015 (1984); Izant, J. G., et al., *Science* 229:345–352(1985) and De Benedetti, A. et al., *Proc. Nat. Acad. Sci.* 84:658–662 (1987)). Possible mechanisms for the antisense effect are the blockage of translation or prevention of splicing, both of which have been observed in vitro. Interference with splicing allows the use of intron sequences (Munroe, S. H., *EMBO. J.* 7:2523–2532 (1988) which should be less conserved and therefore result in greater specificity in inhibiting expression of an enzyme of one species but not its homologue in another species.

By the term "antisense" is intended an RNA sequence, as well as a DNA sequence coding therefor, which is sufficiently complementary to a particular mRNA molecule for which the antisense RNA is specific to cause molecular hybridization between the antisense RNA and the mRNA such that translation of the mRNA is inhibited. Such hybridization must occur under in vivo conditions, that is, inside the cell. The action of the antisense RNA results in specific inhibition of gene expression in the cell. (See: Albers, B. et al., *Molecular Biology of the Cell*, 2nd Ed., Garland Publishing, Inc., New York, N.Y. (1989), in particular, pages 195–196 which reference is hereby incorporated by reference).

According to the present invention, transfection of cells with DNA antisense to the 154 cDNA may inhibit adipocyte differentiation. This antisense DNA must have sufficient complementarity to the p154 gene so that the antisense RNA can hybridize to the p154 gene (or mRNA) and inhibit the gene's expression, regardless of whether the action is at the level of splicing, transcription or translation. The degree of inhibition, readily discernible by one of ordinary skill in the art without undue experimentation, must be sufficient to substantially inhibit adipocyte differentiation. One of ordinary skill in the art will recognize that the antisense RNA approach is but one of a number of known mechanisms which can be employed to block specific gene expression.

The antisense RNA of the present invention may be hybridizable to any of several portions of the target p154 DNA, including the coding sequence, 3' or 5' untranslated regions, or other intronic sequences, or to p154 mRNA. As is readily discernible by one of ordinary skill in the art, the minimal amount of homology required by the present invention is that sufficient to result in hybridization to the p154 DNA or mRNA and inhibition of transcription of the DNA or translation or function or the mRNA, while not affecting the function of other mRNA molecules and the expression of other genes.

Antisense RNA is delivered to a cell by transformation or transfection with a vector into which has been placed DNA encoding the antisense RNA with the appropriate regulatory sequences, including a promoter, to result in expression of the antisense RNA in a host cell, as described herein for expression of other genes.

The present invention is also directed to an antibody specific for an epitope of p154, and the use of such antibody to detect the presence of, or measure the quantity or concentration of the p154 molecule, a functional derivative thereof, or a homologue from a different mammalian species, in a cell, a cell or tissue extract, or a biological fluid.

For use as an antigen for induction of antibodies, the adipocyte polypeptide of the present invention, or functional derivative thereof, preferably having at least 9 amino acids, is obtained and used to immunize an animal for production of a polyclonal antibody or monoclonal antibody (mAb).

An antibody is said to be "capable binding" a molecule if it is capable of specifically reacting with the molecule to thereby bind the molecule to the antibody. The term "epitope" is meant to refer to that portion of any molecule capable of being bound by an antibody which can also be recognized by that antibody. Epitopes or "antigenic determinants" usually consist of chemically active surface groupings of molecules such as amino acids or sugar side chains and have specific three dimensional structural characteristics as well as specific charge characteristics.

An "antigen" is a molecule or a portion of a molecule capable of being bound by an antibody which is additionally capable of inducing an animal to produce antibody capable of binding to an epitope of that antigen. An antigen may have one, or more than one epitope. The specific reaction referred to above is meant to indicate that the antigen will react, in a highly selective manner, with its corresponding antibody and not with the multitude of other antibodies which may be evoked by other antigens.

The term "antibody" is meant to include polyclonal antibodies, monoclonal antibodies (mAbs), chimeric antibodies, and anti-idiotypic (anti-Id) antibodies.

Polyclonal antibodies are heterogeneous populations of antibody molecules derived from the sera of animals immunized with an antigen.

Monoclonal antibodies are a substantially homogeneous population of antibodies to specific antigens. MAbs may be obtained by methods known to those skilled in the art. See, for example Kohler and Milstein, *Nature* 256:495–497 (1975) and U.S. Pat. No. 4,376,110; de St. Groth, S. F. et al., *J. Immunol. Methods*, 35:1–21 (1980); and Hartlow, E. et al., Antibodies: A Laboratory Manual, Cold Spring Harbor Laboratory Press, Cold Spring Harbor, N.Y., 1988). Such antibodies may be of any immunoglobulin class including IgG, IgM, IgE, IgA, IgD and any subclass thereof. The hybridoma producing the mAbs of this invention may be cultivated in vitro or in vivo. Production of high titers of mAbs in vivo production makes this the presently preferred method of production. Briefly, cells from the individual hybridomas are injected intraperitoneally into pristane-primed BALB/c mice to produce ascites fluid containing high concentrations of the desired mAbs. MAbs of isotype IgM or IgG may be purified from such ascites fluids, or from culture supernatants, using column chromatography methods well known to those of skill in the art.

Hybridoma supernatants are screened for the presence of antibody specific for the adipocyte protein of the invention by any of a number of immunoassays, including dot blots and standard enzyme immunoassays (EIA or ELISA), which are well-known in the art. Once a supernatant has been identified as having antibodies, it may be further screened by Western blotting to identify the size of the antigen to which the antibody binds. One of skill in the art will know how to prepare and screen such hybridomas without undue experimentation in order to obtain a desired mAb.

Chimeric antibodies are molecules different portions of which are derived from different animal species, such as those having variable region derived from a murine mAb and a human immunoglobulin constant region. Chimeric antibodies and methods for their production are known in the art (Cabilly et al, *Proc. Natl. Acad. Sci. USA* 81:3273–3277 (1984); Morrison et al., *Proc. Natl. Acad. Sci. USA* 81:6851–6855 (1984); Boulianne et al., *Nature* 312:643–646 (1984);. Neuberger et al., *Nature* 314:268–270 (1985); Taniguchi et al., European Patents Application 171496 (published Feb. 19, 1985); Robinson et al., International Patent Publication #PCT/US86/02269 (published 7 May 1987); Liu et al., *Proc. Natl. Acad. Sci. USA* 84:3439–3443 (1987); Better et al., *Science* 240:1041–1043 (1988)). These references are hereby incorporated by reference.

An anti-idiotypic (anti-Id) antibody is an antibody which recognizes unique determinants generally associated with the antigen-binding site of an antibody. An Id antibody can be prepared by immunizing an animal of the same species and genetic type (e.g. mouse strain) as the source of the mAb with the mAb to which an anti-Id is being prepared. The immunized animal will recognize and respond to the idiotypic determinants of the immunizing antibody by producing an antibody to these idiotypic determinants (the anti-Id antibody).

The anti-Id antibody may also be used as "immunogen" to induce an immune response in yet another animal, producing a so-called anti-anti-Id antibody. The anti-anti-Id may be epitopically identical to the original mAb which induced the anti-Id. Thus, by using antibodies to the idiotypic determinants of a mAb, it is possible to identify other clones expressing antibodies of identical specificity.

Accordingly, mAbs generated against the adipocyte polypeptide of the present invention may be used to induce anti-Id antibodies in suitable animals, such as BALB/c mice. Spleen cells from such immunized mice are used to produce anti-Id hybridomas secreting anti-Id mAbs. Further, the anti-Id mAbs can be coupled to a carrier such as keyhole limpet hemocyanin (KLH) and used to immunize additional BALB/c mice. Sera from these mice will contain anti-anti-Id antibodies that have the binding properties of the original mAb specific for a adipocyte polypeptide epitope.

The anti-Id mAbs thus have their own idiotypic epitopes, or "idiotopes" structurally similar to the epitope being evaluated, such as adipocyte polypeptide-$\alpha$.

The term "antibody" is also meant to include both intact molecules as well as fragments thereof, such as, for example, Fab and $F(ab')_2$, which are capable of binding antigen. Fab and $F(ab')_2$ fragments lack the Fc fragment of intact antibody, clear more rapidly from the circulation, and may have less non-specific tissue binding than an intact antibody (Wahl et al., *J. Nucl. Med.* 24:316–325 (1983)). Such fragments are typically produced by proteolytic cleavage, using enzymes such as papain (to produce Fab fragments) or pepsin (to produce $F(ab')_2$ fragments).

It will be appreciated that Fab and $F(ab')_2$ and other fragments of the antibodies useful in the present invention may be used for the detection and quantitation of adipocyte polypeptide, or for treatment of obesity, according to the methods disclosed herein for intact antibody molecules.

According to the present invention, a subject, preferably a mammalian subject, more preferably a human, suffering from or being susceptible to obesity is treated with an antibody specific for p154 protein to prevent or treat obesity. Such treatment may be performed in conjunction with other anti-obesity therapies, such as, for example, liposuction or lipectomy. Thus, after removal of adipose tissue, treatment with anti-p154 antibody will suppress further adipocyte differentiation, and thereby act to prevent recurrence of obesity A typical regimen for treating obesity comprises administration of an effective amount of the an antibody specific for the p154 protein administered over a period of one or several weeks and including between about one and six months.

The anti-p154 antibody of the present invention may be administered by any means that achieve its intended purpose, preferably to treat obesity in a subject associated with an abnormality in adipocyte differentiation. For example, administration may be by various parenteral routes including, but not limited to, subcutaneous, intravenous, intradermal, intramuscular, and intraperitoneal routes. Alternatively, or concurrently, administration may be by the oral route. Parenteral administration can be by bolus injection or by gradual perfusion over time. Preparations for parenteral administration include sterile aqueous or non-aqueous solutions, suspensions, and emulsions, which may contain auxiliary agents or excipients which are known in the art. Pharmaceutical compositions such as tablets and capsules can also be prepared according to routine methods.

It is understood that the dosage of antibody administered will be dependent upon the age, sex, health, and weight of the recipient, kind of concurrent treatment, if any, frequency of treatment, and the nature of the effect desired. The ranges of effective doses provided below are not intended to limit the inventors and represent preferred dose ranges. However, the most preferred dosage will be tailored to the individual subject, as is understood and determinable by one of skill in the art.

The total dose required for each treatment may be administered by multiple doses or in a single dose. Antibody may be administered alone or in conjunction with other therapeutics directed to the treatment of obesity.

Effective amounts of antibody are from about 0.01 µg to about 100 mg/kg body weight, and preferably from about 10 µg to about 50 mg/kg body weight.

The reaction of the antibodies and the polypeptides of the present invention are detected by immunoassay methods well known in the art (See, for example, Hartlow et al., supra).

The antibodies, or fragments of antibodies, useful in the present invention may be used to quantitatively or qualitatively detect the presence of cells which express the adipocyte polypeptide protein. This can be accomplished by immunofluorescence techniques employing a fluorescently labeled antibody (see below) coupled with light microscopic, flow cytometric, or fluorimetric detection.

The antibodies (of fragments thereof) useful in the present invention may be employed histologically, as in immunofluorescence or immunoelectron microscopy, for in situ detection of the adipocyte polypeptide. In situ detection may be accomplished by removing a histological specimen from a patient, and providing the labeled antibody of the present invention to such a specimen. The antibody (or fragment) is preferably provided by applying or by overlaying the labeled antibody (or fragment) to a biological sample. Through the use of such a procedure, it is possible to determine not only the presence of the adipocyte polypeptide but also its distribution in the examined tissue. Using the present invention, those of ordinary skill will readily perceive that any of a wide variety of histological methods (such as staining procedures) can be modified in order to achieve such in situ detection.

Such assays for adipocyte polypeptide typically comprises incubating a biological sample, such as a biological fluid, a tissue extract, freshly harvested or cultured cells containing adipogenic cells or adipocytes, in the presence of a detectably labeled antibody capable of identifying the adipocyte polypeptide, and detecting the antibody by any of a number of techniques well-known in the art.

The biological sample may be treated with a solid phase support or carrier such as nitrocellulose, or other solid support which is capable of immobilizing cells, cell particles or soluble proteins. The support may then be washed with suitable buffers followed by treatment with the detectably labeled adipocyte polypeptide-specific antibody. The solid phase support may then be washed with the buffer a second time to remove unbound antibody. The amount of bound label on said solid support may then be detected by conventional means.

By "solid phase support or carrier" is intended any support capable of binding antigen or antibodies. Well-known supports, or carriers, include glass, polystyrene, polypropylene, polyethylene, dextran, nylon, amylases, natural and modified celluloses, polyacrylamides, agaroses, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

The binding activity of a given lot of antibody to the adipocyte polypeptide may be determined according to well known methods. Those skilled in the art will be able to determine operative and optimal assay conditions for each determination by employing routine experimentation.

Detection of the adipocyte polypeptide of the present invention or a functional derivative thereof, and of a specific antibody for the polypeptide, may be accomplished using any of a variety of immunoassays well-known in the art, such as enzyme immunoassays (EIA) or radioimmunoassays (RIA).

In an EIA, the antibody can be detectably labeled by linking to an enzyme (See, for example, Voller, A. et al., *Bull. WHO* 53:55–65 (1976); Voller, A. et al., *J. Clin. Pathol.* 31:507–520 (1978); Butler, J. E., *Meth. Enzymol.* 73:482–523 (1981); Maggio, E. (ed), "Enzyme Immunoassay", CRC Press, Boca Raton, Fla., 1980). This enzyme, in turn, when later exposed to an appropriate substrate, will react with the substrate in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection may also be accomplished by visual comparison of the extent of enzymatic reaction of a substrate in comparison with similarly prepared standards.

In an RIA, the antibody may be radioactively labeled. A good description of RIA may be found in *Laboratory Techniques and Biochemistry in Molecular Biology*, by Work, T. S., et al., North Holland Publishing Company, N.Y., (1978) with particular reference to the chapter entitled "An Introduction to Radioimmune Assay and Related Techniques" by Chard, T., incorporated by reference herein. The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labelling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu or others of the lanthanide series. These metals can be attached to the antibody using such metal chelating groups as diethylenetriaminepentaacetic acid (DTPA) or ethylenediaminetetraacetic acid (EDTA).

The antibody also can be detectably labeled by coupling it to a chemiluminescent Compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

The antibody molecules of the present invention may be adapted for utilization in an immunometric assay, also known as a "two-site" or "sandwich" assay. In a typical immunometric assay, a quantity of unlabeled antibody (or fragment of antibody) is bound to a solid support and a quantity of detectably labeled soluble antibody is added to permit detection and/or quantitation of the ternary complex formed between solid-phase antibody, antigen, and labeled antibody.

Typical, and preferred, immunometric assays include "forward" assays in which the antibody bound to the solid phase is first contacted with the sample being tested to extract the antigen from the sample by formation of a binary solid phase antibody-antigen complex. After a suitable incubation period, the solid support is washed to remove the residue of the fluid sample, including unreacted antigen, if any, and then contacted with the solution containing an unknown quantity of labeled antibody (which functions as a "reporter molecule"). After a second incubation period to permit the labeled antibody to complex with the antigen bound to the solid support through the unlabeled antibody, the solid support is washed a second time to remove the unreacted labeled antibody.

In another type of "sandwich" assay, the so-called "simultaneous" and "reverse" assays are used. A simultaneous assay involves a single incubation step as the antibody bound to the solid support and labeled antibody are both added to the sample being tested at the same time. After the incubation is completed, the solid support is washed to remove the residue of fluid sample and uncomplexed labeled antibody. The presence of labeled antibody associated with the solid support is then determined as it would be in a conventional "forward" sandwich assay.

In the "reverse" assay, stepwise addition first of a solution of labeled antibody to the fluid sample followed by the addition of unlabeled antibody bound to a solid support after a suitable incubation period is utilized. After a second incubation, the solid phase is washed in conventional fashion to free it of the residue of the sample being tested and the solution of unreacted labeled antibody. The determination of labeled antibody associated with a solid support is then determined as in the "simultaneous" and "forward" assays.

Antibodies can be used in an immunoaffinity column to purify the adipocyte polypeptide of the invention by a one step procedure, using methods known in the art.

The term "obesity" as used herein is the condition of having a weight which is at least 20% above normal weight for a subject, preferably a human, of given age, sex, and skeletal bone density. There are two classes of obesity. Early onset obesity is characterized by an elevated adipose cellularity (elevated number of adipocytes) and high levels of differentiation (high levels of triglycerides accumulated per cell). Adult onset obesity is often associated with Type II diabetes and is occurring with increasing frequency in middle age populations in industrialized countries. It is characterized mainly by an elevated amount of triglycerides per cell.

In a preferred embodiment, the concentration of the adipocyte polypeptide of this invention is measured in a cell preparation, tissue extract or biological fluid of a subject as a means for determining the susceptibility or the propensity of the subject for obesity. The susceptibility of the subject to obesity is directly proportional to the level of the adipocyte polypeptide.

As disclosed herein, the adipocyte polypeptide is encoded by a mRNA molecule that has a higher level of expression in obese mammals than in their non-obese siblings or littermates. Thus a preferred target cell for performing such an assay is the subject's adipogenic cells, for example, after they have been induced in cell culture to differentiate into adipocytes.

Another embodiment of the invention is evaluating the efficacy of anti-obesity drug or agent by measuring the ability of the drug or agent being evaluated to inhibit the production of the adipocyte polypeptide of this invention by a cell or cell line capable of producing such polypeptides. Preferred cells are cells of an adipogenic cell line undergoing differentiation to become adipocytes. The antibodies of the present invention are useful in the method for evaluating anti-obesity drugs in that they can be employed to determine the amount of the adipocyte polypeptide using one of the above-mentioned immunoassays.

An additional embodiment of the present is directed to assays for measuring the susceptibility of a subject to obesity based on measuring in a tissue or fluid from the subject the amount of the mRNA sequences present that encode p154 or a functional derivative thereof, preferably using an RNA-DNA hybridization assay. The susceptibility to obesity is proportional to the amount of such mRNA sequences present. For such assays, the source of the mRNA sequences is preferably the subject's adipogenic cells, for example, after they have been induced in cell culture to differentiate into adipocytes. The preferred technique for measuring the amount of mRNA is a hybridization assay using DNA of complementary base sequence.

Another related embodiment is a method for measuring the efficacy of an anti-obesity drug or agent which comprises the steps of measuring the agent's effect on adipocyte production of mRNA encoding p154 wherein the efficacy of the drug or agent is proportional to the decrease in the amount of mRNA produced.

Nucleic acid detection assays, especially hybridization assays, can be predicated on any characteristic of the nucleic acid molecule, such as its size, sequence, susceptibility to digestion by restriction endonucleases, etc. The sensitivity of such assays may be increased by altering the manner in which detection is reported or signaled to the observer. Thus, for example, assay sensitivity can be increased through the use of detectably labeled reagents. A wide variety of such labels have been used for this purpose. Kourilsky et al. (U.S. Pat. No. 4,581,333) describe the use of enzyme labels to increase sensitivity in a detection assay. Radioisotopic labels are disclosed by Falkow et al. (U.S. Patent No. 4,358,535), and by Berninger (U.S. Pat. No. 4,446,237). Fluorescent labels (Albarella et al, EP 144914), chemical labels (Sheldon III et al., U.S. Pat. No. 4,582,789; Albarella et al., U.S. Pat. No. 4,563,417), modified bases (Miyoshi et al., EP 119448), etc. have also been used in an effort to improve the efficiency with which detection can be observed.

One method for overcoming the sensitivity limitation of nucleic acid concentration is to selectively amplify the nucleic acid whose detection is desired prior to performing the assay.

Recombinant DNA methodologies capable of amplifying purified nucleic acid fragments have long been recognized. Typically, such methodologies involve the introduction of the nucleic acid fragment into a DNA or RNA vector, the clonal amplification of the vector, and the recovery of the amplified nucleic acid fragment. Examples of such methodologies are provided by Cohen et al. (U.S. Pat. No. 4,237,224), Maniatis, T., et al., etc.

Recently, an in vitro, enzymatic method has been described which is capable of increasing the concentration of such desired nucleic acid molecules. This method has been referred to as the " polymerase chain reaction or "PCR" (Mullis, K. et al., *Cold Spring Harbor symp. Quant. Biol.* 51:263–273 (1986); Erlich H. et al., EP 50,424; EP 84,796, EP 258,017, EP 237,362; Mullis, K., EP 201,184; Mullis K. et al., U.S. Pat. No. 4,683,202; Erlich, H., U.S. Pat. No. 4,582,788; and Saiki, R. et al., U.S. Pat. No. 4,683,194).

The polymerase chain reaction provides a method for selectively increasing the concentration of a particular nucleic acid sequence even when that sequence has not been previously purified and is present only in a single copy in a particular sample. The method can be used to amplify either single—or double-stranded DNA. The essence of the method involves the use of two oligonucleotide probes to serve as primers for the template-dependent, polymerase mediated replication of a desired nucleic acid molecule.

The precise nature of the two oligonucleotide probes of the PCR method is critical to the success of the method. As is well known, a molecule of DNA or RNA possesses directionality, which is conferred through the 5'-3' linkage of the phosphate groups of the molecule. Sequences of DNA or RNA are linked together through the formation of a phosphodiester bond between the terminal 5' phosphate group of one sequence and the terminal 3' hydroxyl group of a second sequence. Polymerase dependent amplification of a nucleic acid molecule proceeds by the addition of a 5' nucleotide triphosphate to the 3' hydroxyl end of a nucleic acid molecule. Thus, the action of a polymerase extends the 3' end of a nucleic acid molecule. These inherent properties are exploited in the selection of the oligonucleotide probes of the PCR. The oligonucleotide sequences of the probes of the PCR method are selected such that they contain sequences identical to, or complementary to, sequences which flank the particular nucleic acid sequence whose amplification is desired. More specifically, the oligonucleotide sequences of the "first" probe is selected such that it is capable of hybridizing to an oligonucleotide sequence located 3' to the desired sequence, whereas the oligonucleotide sequence of the "second" probe is selected such that it contains an oligonucleotide sequence identical to one present 5' to the desired region. Both probes possess 3' hydroxy groups, and therefore can serve as primers for nucleic acid synthesis.

In the polymerase chain reaction, the reaction conditions are cycled between those conducive to hybridization and nucleic acid polymerization, and those which result in the denaturation of duplex molecules. In the first step of the reaction, the nucleic acids of the sample are transiently heated, and then cooled, in order to denature any double-stranded molecules which may be present. The "first" and "second" probes are then added to the sample at a concentration which greatly exceeds that of the desired nucleic acid molecule. When the sample is incubated under conditions conducive to hybridization and polymerization, the "first" probe will hybridize to the nucleic acid molecule of the sample at a position 3' to the sequence to be amplified. If the nucleic acid molecule of the sample was initially doublestranded, the "second" probe will hybridize to the complementary strand of the nucleic acid molecule at a position 3' to the sequence which is the complement of the sequence whose amplification is desired. Upon addition of a polymerase, the 3' ends of the "first" and (if the nucleic acid molecule was double-stranded) "second" probes will be extended. The extension of the "first" probe will result in the synthesis of an oligonucleotide having the exact sequence of the desired nucleic acid. Extension of the "second" probe will result in the synthesis of an oligonucleotide having the exact sequence of the complement of the desired nucleic acid.

The PCR reaction is capable of exponential amplification of specific nucleic acid sequences because the extension product of the "first" probe, of necessity, contains a sequence which is complementary to a sequence of the "second" probe, and thus can serve as a template for the production of an extension product of the "second" probe. Similarly, the extension product of the "second" probe, of necessity, contains a sequence which is complementary to a sequence of the "first" probe, and thus can serve as a template for the production of an extension product of the "first" probe. Thus, by permitting cycles of polymerization, and denaturation, a geometric increase in the concentration of the desired nucleic acid molecule can be achieved. Reviews of the polymerase chain reaction are provided by Mullis, K. B. (*Cold Spring Harbor Symp. Quant. Biol.* 51:263–273 (1986); saiki, R. K., et al. (*Bio/Technology* 1008–1012 (1985)); and Mullis, K. B., et al. (*Met. Enzymol.* 155:335–350 (1987)).

Having now generally described the invention, the same will be more readily understood through reference to the following examples which are provided by way of illustration, and are not intended to be limiting of the present invention, unless specified.

EXAMPLE I

MATERIALS AND METHODS

Animals

Three month-old C57BL/6J mice ob/ob and C57BL/6J A$^y$/a strains from Jackson Laboratories (Bar Harbor, ME) were used for total RNA isolation from different tissues. Two day-old New Zealand Brown rats (NBR) from Trudeau Institute, Saranac Lake, N.Y., were used as a source of adipocyte precursors for primary culture.

Cell Culture 1246 is an adipogenic cell line derived from a C3H mouse teratoma which can proliferate and differentiate in defined medium (G. Serrero et al. (*Anal. Biochem.* 120:351–359 (1982)). Cell culture of 1246 cells in serum-supplemented and serum-free medium was performed as described previously. Total RNA from 1246 preadipocytes were isolated from subconfluent 1246 cells in 10% serum as described below.

1246 cells were cultivated in DME-F12 medium (1:1 mixture) supplemented with bovine insulin (10 μg/ml), human transferrin (10 μg/ml), bovine pituitary basic fibroblast growth factor FGF (25 ng/ml), bovine fetuin (250 μg/ml) and human fibronectin (2 μg/ml). The 1246 cells inoculated at a density of $0.2 \times 10$. cells/cm$^2$, were grown for 4 days in the medium described above. At day 4, when the cells reached confluence, dexamethasone ($2 \times 10^{-7}$M) and 3-isobutyl-1-methylxanthine (2× $10^{-4}$M) and indomethacin (3×$10^5$M) referred to as DEX-MIX-INDO were added to the serum-free medium for 48 hrs. The medium was then replaced by fresh medium without DEX-MIX-INDO and changed every 3 days. The fully differentiated 1246 cells were harvested at day 10 for isolation of RNA. From the results of time course we knew that both glycerol-3-phosphate dehydrogenase mRNA and specific activity reached a maximum level at day 10. The glycerol-3-phosphate dehydrogenase enzymatic assay was performed according to known methods (Wise, L. S. et al., *J. Biol. Chem.* 245:273–275 (1979)).

Primary adipocyte precursors isolated from inguinal fat pads of 48 hr old NBR rats (Serrero, G. *In Vitro Cell. Devel. Biol.* 23:64–66 (1987)) were cultivated in 4F medium consisting of DME-F12 medium (1:1 mixture) supplemented with insulin (10 µg/ml), transferrin (10 µg/ml), fibronectin (2.5 ng/ml), and FGF (25 ng/ml). Cells were harvested and RNA or protein extracted.

Extraction of mRNA from mouse tissues

RNA was extracted from tissues by the guanidine isothiocyanate method (J. M. Chirgwin et al., *Biochemistry* 18.:5294–5299 (1979)). Briefly, cells in the tissue culture dishes were washed with ice-cold PBS before being lysed by 4M guanidinium isothiocyanate. The resulting cell lysate was layered on a 5.7M CsCl cushion and centrifuged at 35,000 rpm for 20 hr at 20.° C. The RNA pellet was collected and its concentration was determined by reading absorbance at 260 nm. Poly(A+)-RNA was isolated by twice oligo(dT)-cellulose (Collaborative Research, Inc.) chromatography (*Proc. Natl. Acad. Sci. USA* 69:1408–1412 (1972)). The method for total RNA isolation from mouse tissues was described by Sambrook et al., supra. Construction and Screening of 1246-Adipocyte cDNA Library cDNA was synthesized for poly(A+)-RNA from 1246 adipocytes collected 5 days post—confluence using well known methods (Gubler, V. et al., *Gene* 25:263–269 (1983); Cochran, B. H. et al., Methods Enzymol. 147:64–85 (1987)). Enzymes involved in cDNA synthesis were purchased from BRL. EcoRI linkers (New England Bioresearch) were blunt-end ligated onto methylated cDNA by using T4–ligase (Stratagene). After EcoRI digestion to generate cohesive ends, the cDNA was separated from excess linkers by Sepharose 4B (Pharmacia) chromatography then the cDNA was ligated. into EcoRI digested-phosphatase treated ZAP arms (Stratagene) and packed in vitro using Gigapack™ (Stratagene) using methods described by manufacturer's instructions. The cDNA library contained 1.6×$10^6$ recombinants.

Approximately 4×$10^4$ ZAP recombinant phages were screened using *E. coli* BB4 (Stratagene) as ZAP host and phage plaques were transferred to nitrocellulose filters (Schleicher and Schuell) as described in the Stratagene manual. Duplicate sets of filters were hybridized for 24 hr at 42° C. with $^{32}$P-labeled cDNA (4×$10^5$ cpm/ml) synthesized from poly(A+)-RNA of 1246 preadipocytes which were grown in 10% FBS and poly(A+)-RNA of 1246 adipocytes which were differentiated in defined medium. Phage plaques that preferentially hybridized to the cDNA made from adipocyte poly(A+)RNA were selected for further analysis. Dot blotting analysis was performed for second round screening using both preadipocyte and adipocyte probes. Phagemids, Bluescript SK(–) containing cDNA inserts, were obtained from the ZAP clones specific to the adipocyte cDNA probe after the automatic excision process (Short, J. M. et al., *Nucl. Acids Res.* 16:7583–7600 (1988)) for further characterization of the clones.

Southern cross-hybridization analysis

Bluescript phagemids obtained from automatic excision processes were used to transform *E. coli* BB4 cells and plasmid DNA of each adipocyte specific clone was isolated (Birnboim, H. C. et al. Nuc. Acid Res. 1513–1523 (1979)).

For each southern analysis, plasmid DNA was digested with EcoRI (BRL) and loaded in an agarose gel for electrophoresis. After electrophoresis, DNA in the gel was denatured, neutralized and transferred to a nitrocellulose filter. The filter was baked at 80° C. under vacuum for 2 hr, prehybridized at 42° C. and then hybridized to nick translated cDNA insert of each clone at a concentration of 4×$10^5$ cpm/ml.

Northern Analysis

Five to fifteen micrograms of total RNA was size fractionated by agarose gel electrophoresis under denaturing conditions and transferred to nitrocellulose filters (Lehrach, H. et al., *Biochemistry* 16:4743–4751 (1977); Seed, B., In: *Genetic Engineering: Principles and Methods* (Setlow, J. K., ed.), Plenum Publishing, N.Y. 4:91–102 (1982)). Nitrocellulose filters were baked at 80° C. under vacuum for 2 hrs and then prehybridized at 42° C. for a minimum of 4 hrs. Nick translated cDNAs (specific activity 1–2×$10^8$ cpm/µg) of clones 79, 97, 117, 154, 168 and 176 as well. as G3PDH were used as probes (2×$10^6$ cpm/ml hybridization solution). After hybridization filters were washed and exposed as described in the following. The nick translation kit was purchased from BRL. G3PDH cDNA (Kozak, L.P. et al., *Proc. Natl. Acad. Sci. USA* 80:3020–3024 (1983)) was kindly provided by Dr. Leslie Kozak (Jackson Laboratories, Bar Harbor, ME), Hybridization and washing. conditions Both prehybridization and hybridization solutions contain 50% formamide, 5X Denhardt's solution, 5X SSPE, 0.1% SDS, 1 µg/ml poly-A and 100 µg/ml sheared salmon sperm DNA as described (27). The hybridization solution contained the appropriate $^{32}$P-labelled cDNA probe. After hybridization for 24 hrs the filters were first washed with 0.1×SSC (1×SSC=0.15M NaCl, 0.015M sodium citrate, pH 7.5) and 0.1% SDS at room temperature for 5 min and then twice with the same washing buffer at 42° C. for 30 min. The dried filters were exposed to Kodak XAP-5 film with intensifying screens (DuPont) at –70° C.

EXAMPLE II

Isolation of cDNA Clones Corresponding to mRNAs Induced During Differentiation of 1246 Cells A cDNA library of approximately $10^6$ recombinants was generated in the ZAP vector as described in Example I. About 40,000 independent recombinants were screened by differential hybridization using $^{32}$P-labeled cDNAs made from mRNA isolated from 1246 cells prior to and after adipogenic conversion and hybridized to a parallel set.of filters containing phage DNA as described in Example I. As shown in FIG. 1, most clones gave signals having the same intensity when being hybridized to radiolabeled cDNAs from preadipocytes or adipocytes. This indicates that the level of these mRNAs did not change during adipogenesis of 1246 cells. Two hundred eighty clones showed stronger signals when hybridized to cDNAs from differentiated 1246 cells than they did with cDNAs from un differentiated cells.

The second round of screening was done by dot blotting parallel sets of filters containing phage DNA and hybridizing them as described above. Eighty five clones reacted more strongly with adipocyte cDNA. These 85 clones were converted to phagemids by the automatic excision process as detailed by Short et al. (supra). Several phagemid DNAs were isolated and insert purified. To characterize these cDNA clones, the purified inserts were radiolabeled to high specific activity by nick translation and hybridized to nitrocellulose filters containing equal amounts of total RNA isolated from 1246 cells before and after differentiation. The nick translated probes were also hybridized to Southern filters containing the DNA of the 85 clones obtained from the second round of screening to rule out clones with the same cDNA.

Described herein are the characteristics of 6 clones obtained by this approach. Five of these clones correspond to mRNAs which are increased during adipogenesis of the 1246 cells whereas one of them showed decreased mRNA expression during differentiation (FIG. 2). The size of the cDNA clones isolated and of the mRNA to which they hybridize is provided in Table 1, below.

TABLE 1

Characteristics of Differentiation-Inducible cDNA Clones in 1246 Cells

| Clone | cDNA size[a] (kb) | mRNA size[b] (kb) | Increase During During Adipogenesis[c] |
|---|---|---|---|
| 154 | 0.8 | 2.2 | >100-fold |
| 117 | 2.1 | 4.5 | >100-fold |
|  |  | 2.2 |  |
| 97 | 0.35 | 0.7 | >100-fold |
| 177 | 0.62 | 1.1 | >3-fold |
| 76 | 1.3 | 1.4 | 3–4-fold |
| 168 | 0.6 | 0.8 | Decreased 2-fold |

[a]Size of the cDNAs was determined by electrophoresis on 1.1% agarose gel.
[b]Size of mRNA was estimated by northern blot analysis of formaldehyde agarose gels as described in Example I using 28S and 18S ribosomal RNA as standards.
[c]The fold increase (or decrease) was determined by scanning densitometry of undifferentiated and differentiated clone-specific RNA.

The sizes of the transcripts varied from 700 to 4500 bases. Northern blot hybridization of the 6 clones to mRNA isolated from differentiated 1246 cells (lane A) and from undifferentiated cells (lane B) indicates that there are differences not only in the absolute abundance of the inducible transcripts but also in their relative increase in the concentration during differentiation. Based on the results of FIG. 2, the cDNA clones isolated were classified into three groups: Group I contained clones corresponding to mRNA transcripts increasing 100-fold or more during adipogenesis of 1246 cells (clone 154, 97 and 117); Group II included clones 76 and 177 corresponding to transcripts increasing to 3- to 4-fold; and Group III included clone 168 which corresponds to a transcript that is 3-fold lower in differentiated than in undifferentiated cells. The experiments described below concern exclusively clones belonging to group I.

Two of the cDNA clones of group I could be identified by using direct DNA sequencing method. Clone 97 encoded a protein which was homologous to amino acid residues 75 to 130 of the 13 kDa fatty acid binding protein p422 which has been isolated in several laboratories (Chapman, A. B., et al., *J. Biol. Chem.* 259:15548–15555 (1984); Spiegelman, B. M. et al., *J. Biol. Chem.* 258:10083–10089 (1983); Bernlohr, D. A. et al., *Proc. Natl. Acad. Sci. USA* 81:5468–5472 (1984)). The DNA sequence of Clone 117 was homologous to lipoprotein lipase isolated from mouse macrophages (Kirchgessner, T. G. et al., *J. Biol. Chem.* 262:8463–8466 (1987)). Interestingly, clone 117 was a full length cDNA and encoded the complete sequence for the entire precursor molecule which had been hypothesized by Kirchgessner et al. (supra) based on the sequence of the human lipoprotein lipase (Wion, K. L. et al., *Science* 235:1638–1641 (1987)). Direct sequencing of p154 cDNA revealed no homology with sequence's in GenBank or in PIR protein databases. Using a probe for the enzyme glycerophosphate dehydrogenase first isolated by Kozak et al. (supra), the present inventor was unable to identify a hybridizing clone among the recombinants picked although this enzymatic activity is abundant in adipogenic cell lines including 1246. This indicates that the relative abundance of mRNA is not always reflected by the relative abundance of the complementary cDNA in a recombinant library.

EXAMPLE III

Temporal Expression of RNAs Induced During Differentiation of 1246 cells

The 1246 cells were cultivated in defined medium as described in the Example I. At day 4, when the cells reached confluence, they were treated for 48 hrs with dexamethasone ($10^{-6}$M), isobutylmethylxanthine ($2\times10^4$M) and indomethacin ($3\times10^5$M) which are used as accelerators of differentiation. Differentiation was followed by measuring the level of glycerol-3-phosphate dehydrogenase (G3PDH) specific activity which is a late marker of differentiation. As shown in FIG. 3, the level of G3PDH specific activity started to increase at day 8 (2 days after the end of the 48 hr stimulation) and peaked at day 10.

Figure 4:
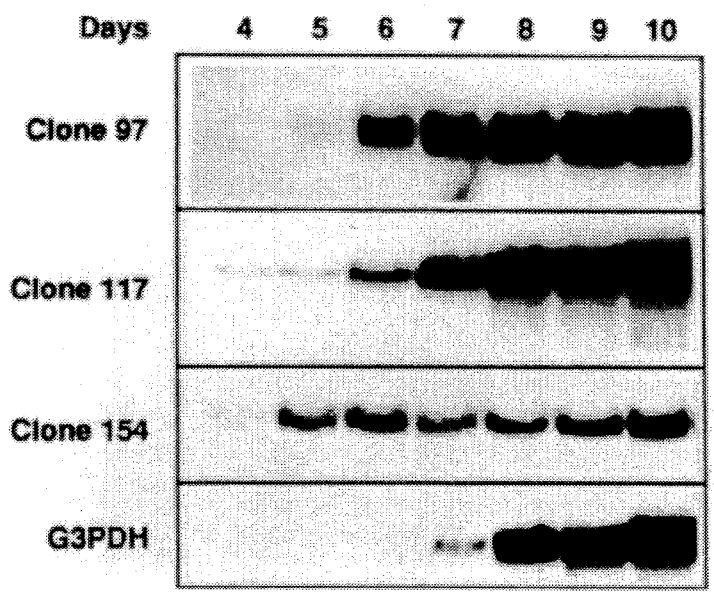
FIG. 4 shows a northern blot indicating the expression of specific mRNA during adipogenesis of 1246 cells. Cells were treated as in FIG. 3. Total RNA, collected every day starting at day 4, was loaded onto each lane of a 1.4% agarose gel containing formaldehyde.

Total RNA of 1246 cells was extracted from cells collected daily day starting at day 4 in order to examine the temporal expression of the transcripts for the clones of Group I. The results of a typical northern analysis is shown in FIG. 4. RNA complementary to clone 154 was present at very low levels in the confluent cells. One day after stimulation with DEX-MIX-INDO, large amounts of RNA accumulated and remained constant throughout the course of the experiment. Individuals filters washed free of clone 154 cDNA were analyzed with cDNA from the other clones in a sequential fashion in order to prevent the variation between different tissue culture experiments. The mRNA complementary to clone 117 began increasing at day 6 (when the DEX-MIX-INDO was removed). Maximum expression of 117 mRNA was day 8. The mRNA complementary to clone 97 was not expressed in confluent 1246 cells but appeared at a low level 24 hrs after DEX-MIX-INDO treatment. It reached a plateau at day 8. G3PDH mRNA, used as a late marker, reached a maximum 4 days after DEX-MIX-INDO removal.

Based on these results, it is clear that the 154 mRNA content of differentiated 1246 cells increases 1 day prior to the increase of lipoprotein lipase and fatty acid binding protein mRNAs and reached a maximal level at a time when mRNA for G3PDH was still increasing. Fatty acid binding protein and lipoprotein lipase are considered as early markers of adipogenesis for many of the cell lines examined (Amri, E. Z. et al., *Biochem. Biophys. Res. Commun.* 137:903–910 (1987)). This suggests that clone 154 represents a very early marker of adipose differentiation.

EXAMPLE IV

Figure 5:
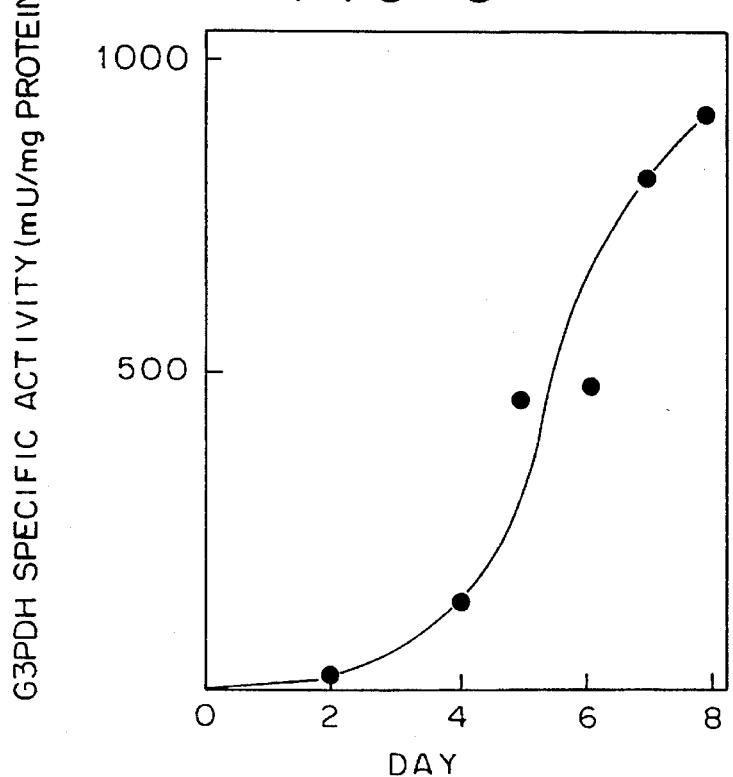
FIG. 5 is a graph showing an increase in G3PDH specific activity during adipose conversion of adipocyte precursors in primary culture.

Expression of Specific mRNAs During Differentiation of Adipocyte Precursors in Primary Cultures The expression of clone 154 mRNA in adipocyte precursors freshly isolated from rat inguinal fat pads was next examined. The laboratory of the present inventor has found that adipocyte precursors isolated from inguinal fat pads of 48-hr old rats could be cultured in defined medium designated 4F. The 4F medium consists of DME-F12 medium (1:1 mixture) supplemented with fibronectin, insulin, transferrin and fibroblast growth factor (Serrero, G. *In Vitro cell. Devel. Biol.* 23: 64–66 (1987)). Under these conditions, the cells proliferate and differentiate as shown by the increase in G3PDH specific activity (FIG. 5). At day 5, G3PDH specific activity is approximately half of the day 8 maximum level. Total RNA was extracted from cells starting at day 2 after inoculation, and daily from day 4 to 8. Fifteen μg of total RNA was used for northern analysis which was performed in order to examine the temporal expression of mRNAs for clone 154, 117 and 97.

Figure 6:
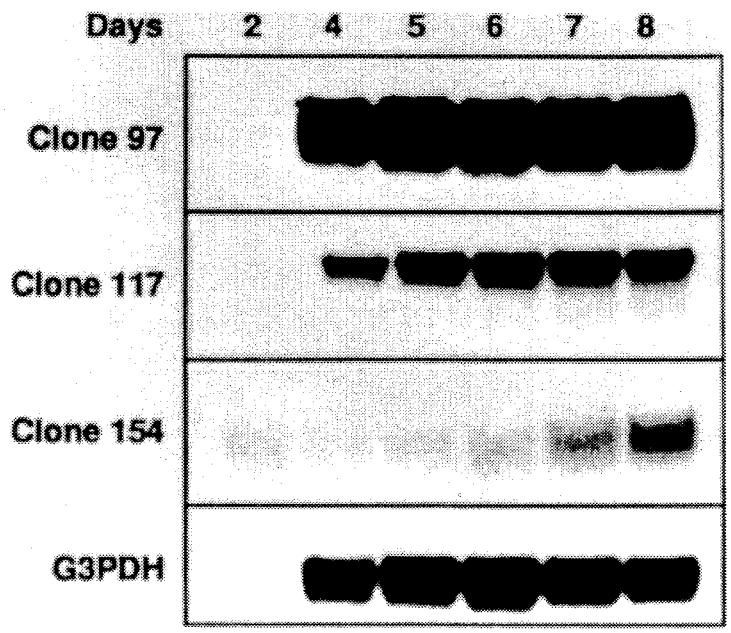
FIG. 6 is a northern blot showing expression of specific mRNAs during adipose conversion of primary cultured adipocyte precursors. Total RNA, collected on day 2 and days 4–8 after initiation of culture, was loaded onto each lane and the northern analysis performed.

As with 1246 cells, clone 154 mRNA was the first to be induced, and was detectable as early as day 2 (FIG. 6). In contrast, 154 mRNA level which remained constant from days 2–6 in 1246 cells increased further at day 6, peaking at day 8. The kinetics of appearance of clone 97 and 117 mRNAs were different. These mRNAs were first apparent at day 4 and reached a maximum at day 6. The time course of induction of G3PDH mRNA paralleled that of clone 97.

EXAMPLE V

Hormonal Control of 154 mRNA Expression 1246 Cells

To ascertain whether the induction of clone 154 mRNA was related to the onset of differentiation of 1246 cells, it was investigated if the increase of 154 mRNA content of the cells was prevented by treatment with known inhibitors of adipose differentiation such as transforming growth factor-β (TGF-β) and tumor necrosis factor-α (TNF-α). TNF-α and TGF-β were shown to inhibit the expression of mRNA encoding proteins which are considered adipose differentiation markers: lipoprotein lipase, fatty acid binding protein, G3PDH and pOb24 (Amri, E. Z. et al., *Biochem. Biophys. Res. Commun.* 137:903–910 (1987); Torti, F. M. et al., *J. Cell Biol.* 108:1105–1113 (1989)).

Figure 7:
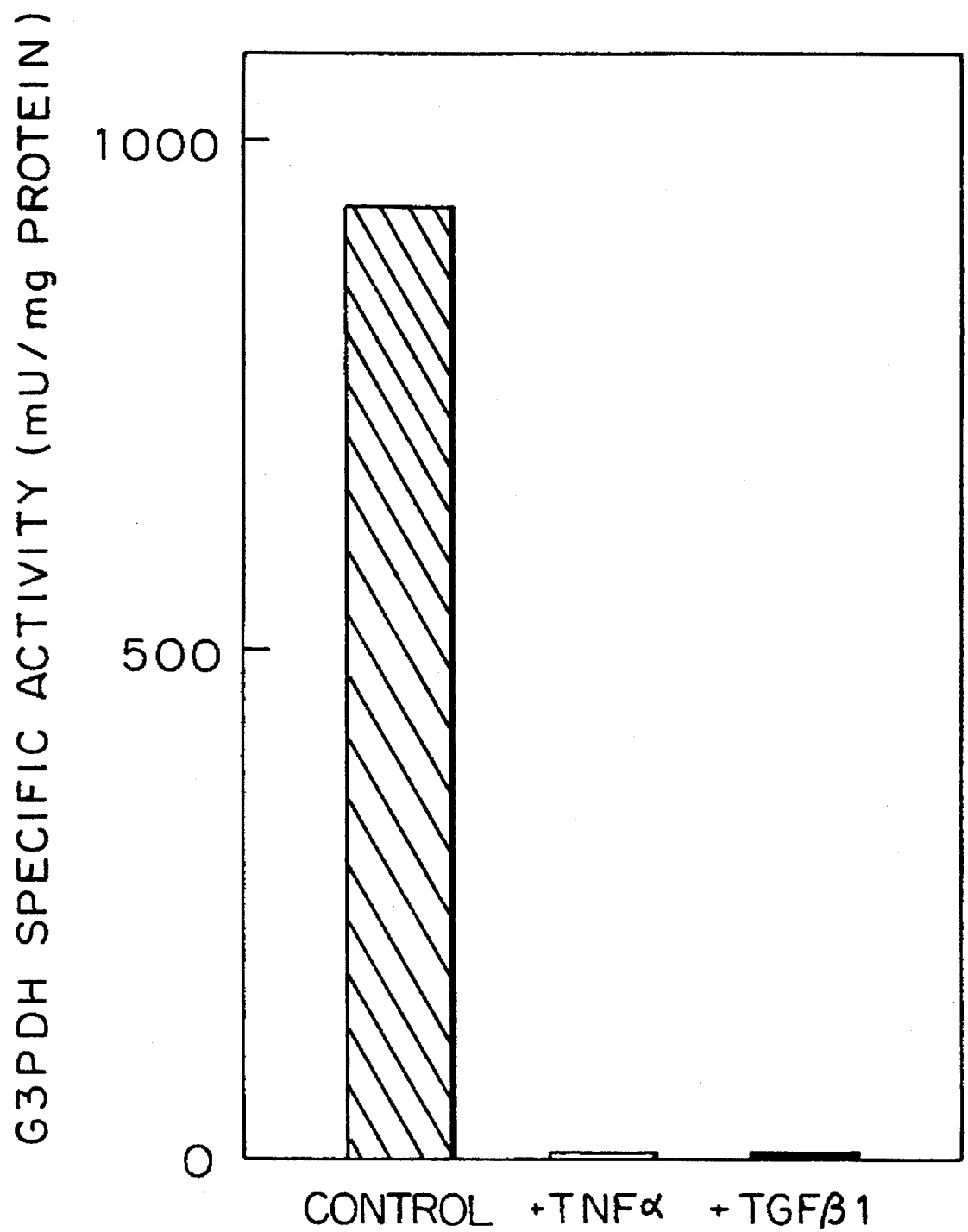
FIG. 7 is graph showing the effect of TNF-α (10 ng/ml) and TGF-β(1 ng/ml) on the increase of G3PDH specific activity.
Figure 8:
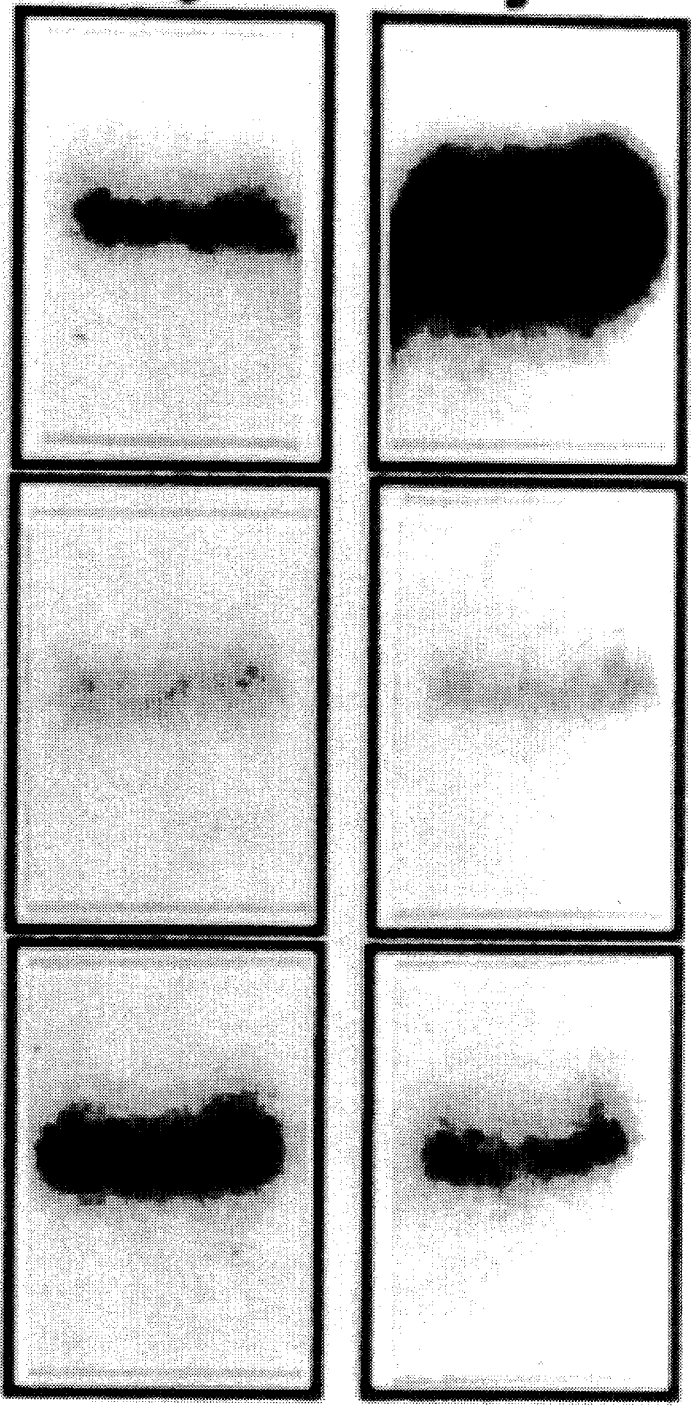
FIG. 8 is a northern blot showing the effect of TNF-α (10 ng/ml) and TGF-β (1 ng/ml) on the expression of p154 mRNA. Cells were assayed on days 4 and 12.
Figure 9:
FIG. 9 is a northern blot showing the tissue distribution of mRNA expression of several p154 clones. Total RNA from mouse kidney, liver, heart, brain and inguinal fat pad were tested.

As shown in FIG. 7, treatment of 1246 cells with 10 ng/ml TNFα or 1 ng/ml TGFβ caused maximal inhibition of differentiation, manifest as very low levels of G3PDH enzymatic activity in both treated cells compared to untreated controls. As shown in FIG. 8, TNFα or TGFβ caused a maximal inhibitory effect on the expression of clone 154 mRNA. In fact, when compared to the 154 mRNA level on day 4 (in treated or untreated cells) the level at day 12 did not increase in the presence of either TNFα or TGFB, whereas the day 12 level in control cells was greatly increased at day 12.

Epidermal growth factor (EGF) which inhibits the differentiation of 1246 cells also caused a 50% reduction in 154 mRNA.

EXAMPLE VI

Tissue-Specific Expression of p154 In Vivo

Total RNA from mouse kidneys, brain, heart, liver and inguinal fat pad were isolated in order to examine the in vivo expression of mRNA coded by the clones. Northern blot analysis indicated that clone 117 mRNA was expressed at high levels in inguinal fat pad, heart and at a lower level in kidney. This tissue distribution was expected given that clone 117 is complementary to lipoprotein lipase (Wion, K. L. et al., *Science* 235:1638–1641 (1987)). The fact that clone 97 was expressed only in fat pad is in agreement with the results of others (Bernlohr, D. A. at al. *Biochem. Biophys. Res. Commun.* 132:850–855 (1985)) showing the specific location of fatty acid binding protein in adipose tissue. Interestingly, p154 mRNA was expressed exclusively in adipose tissue, suggesting that the p154 protein is adipose tissue specific.

EXAMPLE VII

Expression of p154 mRNA In Vivo in Obesity

C57BL/6J Ob/Ob mice aged 4 to 16 weeks and their normal littermates. (C57BL/6J Ob/+ or C57BL/6J +/+) were weighed prior to sacrifice. Inguinal fat pads (from males and females), epididymal fat pads (from males), ovarian fat pads (from females), were collected, quick frozen in liquid nitrogen for RNA extraction (Chirgwin et al., supra). Expression of p154 mRNA was investigated by Northern blot analysis. Quantitation of mRNA expression for 154 was done by dot blot hybridization.

The results showed a 3-fold (for 4 week old mice) to 10-fold (for 12 week old animals and older) higher level of p154 mRNA in obese animals as compared to normal littermates. Notably, the increase in obese animals was detectable very early in life when obesity was just becoming apparent. Similar results were obtained using another obese mouse strain, Yellow ($A^y$) and with diabetic db/db mice.

These results indicate that p154, a protein associated with adipocyte differentiation, may be synthesized at higher levels in genetically obese animals than in normal mice.

EXAMPLE VIII

ISOLATION. OF A HUMAN cDNA PROBE FOR p154

A. Human Fat Cell cDNA Library Screening

A human fat cell lambda gt11 cDNA library was purchased from Clontech and titered. The phage, at 100,000 pfu, were mixed with host cells of the *E. coli* strain Y1090 and plated on 22.5 cm×22.5 cm dishes (NUNC, Thomas Scientific) for a total of 400,000 pfu screened. The infected cells were incubated overnight at 37° C. and chilled for 2 hr at 4° C. Plaques wire sampled by double lifts using Nitro Plus (MSI, Fisher). A 405 bp cDNA including the 5' end of mouse p154 was random primed (Boehringer-Mannheim) with $^{32}P$ and hybridized overnight in 50% formamide hybridization solution for 18 hours with filters. The filters were washed once in 1×SSC, 0.1% SDS for 30 min at 42° C., 3 times in 0.2×SSC, 0.1% SDS, twice for 30 min each and once for 1 hr at 42° C., air dried and exposed to X-ray film overnight at −70° C. with an intensifying screen. Four positive clones were picked. Through plaque purification, it was found that only two were true positives, and included a 300 bp insert and a 540 bp insert. The phage was isolated by standard procedures (Sambrook et al., supra), the cDNA insert cut out, gel purified, and isolated using Millipore 0.45 μm ULTRAFREE-MC filter units. The insert was subcloned into pGEM −3zf(−) plasmid (purchased from Promega) and transformed into DH5 subcloning efficiency cells (Life Technologies, Inc., Gaithersburg, Md.). LiCl minipreps (He et al., *Nucl. Acid Res.* 18:1660 (1990)) were performed to identify the appropriate clones, and production was scaled up to a 20 ml preparation.

B. Sequencing of cDNA

The DNA was isolated by the LiCl method, and the pellet was dissolved in 25 µl distilled water. Sequencing was done on an ABI 370A automated sequencer with fluorescently labeled dye primers.

Clone B5B yielded DNA of 540 bp of which 474 bp contained the coding region of the human p154 DNA (SEQ ID NO:3). Homology with the mouse p154 cDNA started at amino acid 50 and continued through amino acid 197 with 79% homology (FIG. 10).

EXAMPLE IX

CONSTRUCTION AND EXPRESSION OF A VECTOR ENCODING A MOUSE p154 FUSION PROTEIN

Figure 11:
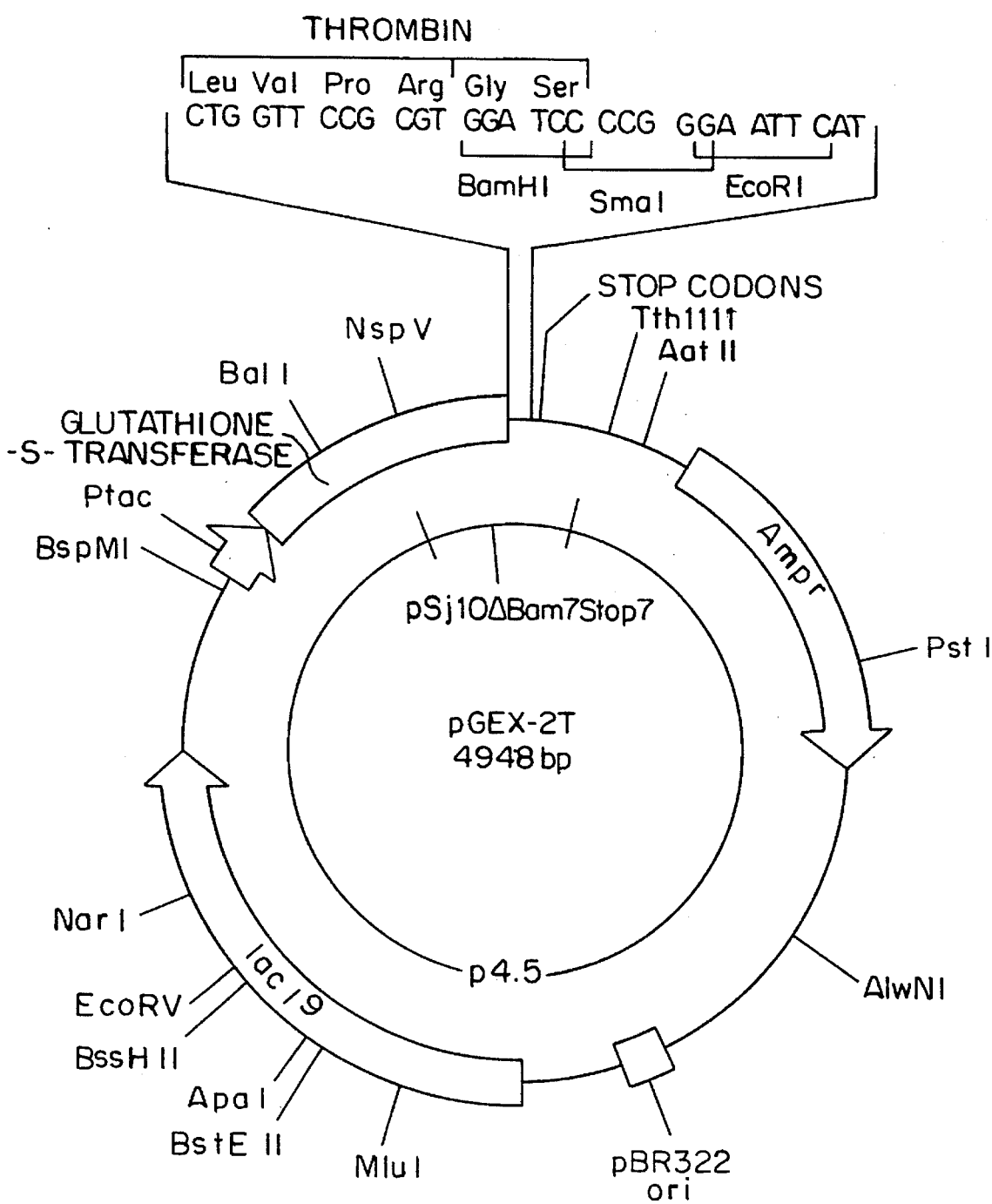
FIG. 11 is a diagram of the vector used to express the human p154 cDNA fusion protein.

These experiments were performed using a cDNA probe to clone mouse p154 containing the entire open reading frame (425 amino acids)(clone 154). Clone 154 was cloned into the EcoRI site of PGEX-2T vector obtained from Pharmacia, and illustrated in FIG. 11.

The use of this vector allows the expression of a fusion protein of p154 with glutathione-S-transferase.

The procedure for cloning 154 cDNA into the PGEX-2T vector was described by Smith, D. B. et al. (*Gene* 67:31–40 (1988)) and specified in the instructions provided by the manufacturer. HB101 competent cells were transformed with plasmids. After miniprep, the plasmid containing the cDNA having the proper orientation was chosen by restriction mapping using the PStI restriction enzyme. The cDNA encoding p154 was inserted into the plasmid in the same reading frame as glutathione-S-transferase (GST) by using the restriction enzyme AvaI followed by treatment with S1 nuclease and T4 ligase. PGEX-2T has one AvaI site at position 935 whereas clone 154 cDNA has none. Sequencing of the fusion plasmid is used to confirm the correct sequence of the proper reading frame.

Expression of the fusion protein was carried out according to Smith, D. B. et al. (Gene 67:31–40 (1988)) and to the manufacturer's instructions, except that isopropyl-β-D-thiogalactoside (IPTG) was added at a final concentration of 1 mM 1 hr before harvesting the cells in order to induce the expression of the fusion protein. This was done because the fusion protein is not stable when expressed by the cells. Cell extraction was performed in the presence of protease inhibitors pepstatin A (1 µg/ml), leupeptin (1 µg/ml) and PMSF (7 µg/ml) added to the lysis buffer (PBS, pH 7.4, containing 1% Triton X-100). Cells were lysed by mild sonication, and the crude extract was centrifuged at 10,000×g for 5 min at 4° C.

SDS-PAGE analysis was used to verify that the fusion protein was present in the supernatant and not in the cell pellet, indicating that the fusion protein was soluble. The supernatant was used for subsequent purification of the fusion protein. Chromatography on a glutathione-Sepharose 4B affinity column allows a rapid single step purification of recombinant derivatives of glutathione-S-transferase due to affinity of the protein to its substrate, glutathione. The fusion protein was eluted by a buffer containing 5 mM glutathione in 50 mM Tris-HCl, pH 8.0. Eluted fractions were examined for the presence of the fusion protein by SDS-PAGE analysis.

The gel pattern indicated that a 75 kDa fusion protein had been retained on the column and eluted by the elution buffer. This apparent molecular weight was compatible with the predicted size of the fusion protein between glutathione-S-transferase (26 kDa) and the p154 clone.

EXAMPLE X

ANTIBODIES TO p154 AND THEIR USE TO DETECT p154 IN DIFFERENTIATING CELLS

A. Immunization

Rabbits were injected with the affinity purified fusion protein which had been denatured either by treatment with 8M urea or by heat. A dose of 100–150 µg of fusion protein was injected per rabbit. The antigen was emulsified with RIBI adjuvant (MPL+TDM+CWS emulsion) from RIBI Immunochem, prepared according to the manufacturer's instructions. Each rabbit received the antigen in a total volume of 1 ml dose administered as follows: 0.2 ml intraperitoneally, 0.4 ml subcutaneously, 0.2 ml intramuscularly and 0.2 ml intradermally. The first booster injection was given 21 days later. Rabbits were test bled and their serum tested for antibodies. Booster injections were repeated at 15 day intervals followed by a test bleed 1 week after each booster injection.

B. Assay of Anti-p154 Antibodies

Serum samples were tested in ELISA to determine the antibody titer using the fusion protein as the test antigen. In general, 0.5 µg/ml of antigen in 0.05M $NaHCO_3$ pH 9.6 were incubated at 4° C. overnight. In the case of fusion protein, ELISA were also performed with plates coated with GST only to make sure that antisera recognized the fusion protein or the 154 protein rather than GST alone. Antisera collected from rabbits injected with fusion protein will be applied to glutathione-S-transferase column to remove anti-GST antibodies.

Sera positive for the fusion protein were tested for their ability to recognize p154 in 1246 cells undergoing differentiation. 1246 cells were plated in defined medium (see above). At day 4, cells were treated for 48 hrs with dexamethasone ($2\times10^{-6}$M), isobutylmethylxanthine ($2\times10^{-4}$M) and indomethacin ($3\times10^{-5}$M) (DEX-MIX INDO). At day 6, medium was replaced with fresh defined medium deprived of DEX-MIX INDO. Cells were harvested at days 4, 5, 6 and 12. Cell extracts were prepared by adding 200 µl of 2× SDS-PAGE sample buffer per dish containing 2-mercaptoethanol. Cell extract was boiled and centrifuged 13,000 rpm×10 min at 4° C. prior to being applied to 10% SDS-PAGE. An amount of protein equivalent to 50,000 cells was applied per lane. Proteins were electroblotted onto "Immobilon P" membranes (Millipore). Membranes were incubated with a 1/200 dilution of the anti-p154 fusion protein antiserum followed by a secondary goat anti-rabbit immunoglobulin antibody conjugated to alkaline phosphatase followed by color development according to standard procedures.

Figure 12:
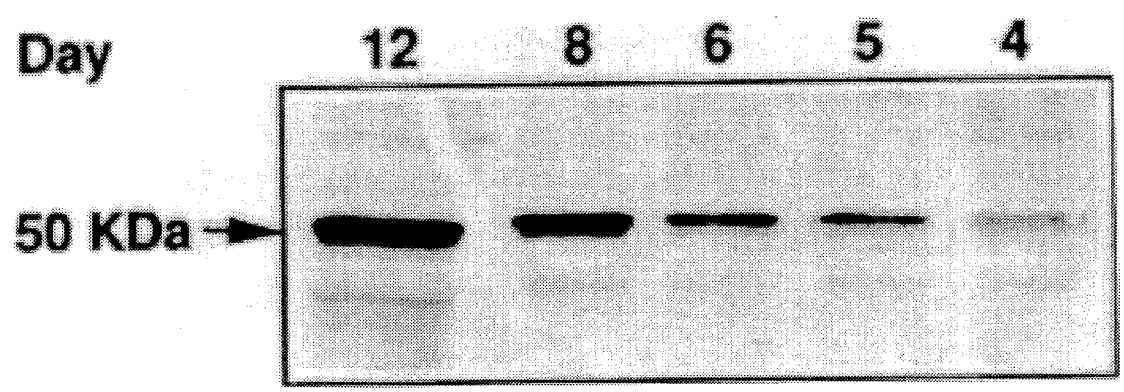
FIG. 12 is a gel pattern of a Western blot showing the immunodetection of p154 in 1246 cells undergoing differentiation.

This Western blot analysis of 1246 cell extracts showed that the antiserum specifically recognized a single band corresponding to a protein having an apparent molecular weight of 50 kDa, which increased in quantity as the cells differentiated (FIG. 12). The molecular mass of the cellular protein is compatible with that predicted from the deduced amino acid sequence determined from the nucleotide sequence of p154 full length cDNA (SEQ ID NO:2). No proteins were detected in duplicate blots reacted with a non-immune rabbit serum.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 1685 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 79..1353

( x i ) SEQUENCE DESCRIPTION: SEQ ID NO:1:

```
TAGTGGTGAT CTGGACCGTG CGGACTTGCT CGTCCCTCAG CTCTCCTGTT AGGCGTCTCT        60

TTTCTCCAGG AGGAAAAA ATG GCA GCA GCA GTA GTG GAT CCG CAA CAG AGC        111
                    Met Ala Ala Ala Val Val Asp Pro Gln Gln Ser
                     1               5                   10

GTG GTG ATG AGA GTG GCC AAC CTG CCC TTG GTG AGC TCT ACC TAC GAC        159
Val Val Met Arg Val Ala Asn Leu Pro Leu Val Ser Ser Thr Tyr Asp
             15                  20                  25

CTT GTG TCC TCC GCT TAT GTC AGT ACA AAG GAT CAG TAC CCG TAT TTG        207
Leu Val Ser Ser Ala Tyr Val Ser Thr Lys Asp Gln Tyr Pro Tyr Leu
         30                  35                  40

AGA TCC GTG TGT GAG ATG GCC GAG AAG GGC GTG AAG ACC GTG ACC TCT        255
Arg Ser Val Cys Glu Met Ala Glu Lys Gly Val Lys Thr Val Thr Ser
     45                  50                  55

GCG GCC ATG ACA AGT GCC CTG CCC ATC ATC CAG AAG CTG GAG CCA CAA        303
Ala Ala Met Thr Ser Ala Leu Pro Ile Ile Gln Lys Leu Glu Pro Gln
 60                  65                  70                  75

ATT GCG GTT GCC AAT ACC TAT GCC TGC AAG GGG CTA GAC AGG ATG GAG        351
Ile Ala Val Ala Asn Thr Tyr Ala Cys Lys Gly Leu Asp Arg Met Glu
                 80                  85                  90

GAA AGA CTG CCT ATT CTG AAC CAG CCA ACG TCC GAG ATT GTT GCC AGT        399
Glu Arg Leu Pro Ile Leu Asn Gln Pro Thr Ser Glu Ile Val Ala Ser
             95                 100                 105

GCC AGA GGT GCC GTA ACT GGG GCG AAG GAT GTG GTG ACG ACT ACC ATG        447
Ala Arg Gly Ala Val Thr Gly Ala Lys Asp Val Val Thr Thr Thr Met
         110                 115                 120

GCT GGA GCC AAG GAT TCT GTA GCC AGC ACA GTC TCA GGG GTG GTG GAT        495
Ala Gly Ala Lys Asp Ser Val Ala Ser Thr Val Ser Gly Val Val Asp
     125                 130                 135

AAG ACC AAA GGA GCA GTG ACT GGC AGC GTG GAA AGG ACC AAG TCT GTG        543
Lys Thr Lys Gly Ala Val Thr Gly Ser Val Glu Arg Thr Lys Ser Val
140                 145                 150                 155

GTC AAT GGC AGC ATC AAT ACA GTT TTG GGG ATG GTG CAG TTC ATG AAC        591
Val Asn Gly Ser Ile Asn Thr Val Leu Gly Met Val Gln Phe Met Asn
                 160                 165                 170

AGT GGA GTA GAT AAT GCC ATC ACC AAG TCG GAG ATG CTG GTA GAC CAG        639
```

```
        Ser Gly Val Asp Asn Ala Ile Thr Lys Ser Glu Met Leu Val Asp Gln
                    175                 180                 185

TAC TTC CCT CTC ACT CAG GAG GAG CTG GAG ATG GAA GCA AAA AAG GTG              687
Tyr Phe Pro Leu Thr Gln Glu Glu Leu Glu Met Glu Ala Lys Lys Val
        190                 195                 200

GAA GGA TTT GAT ATG GTT CAG AAG CCG AGC AAC TAT GAA CGG CTG GAG              735
Glu Gly Phe Asp Met Val Gln Lys Pro Ser Asn Tyr Glu Arg Leu Glu
        205                 210                 215

TCC CTG TCT ACC AAG CTC TGC TCT CGG GCT TAT CAC CAG GCT CTC AGC              783
Ser Leu Ser Thr Lys Leu Cys Ser Arg Ala Tyr His Gln Ala Leu Ser
220                 225                 230                 235

AGG GTT AAA GAG GCC AAA CAA AAG AGC CAG GAG ACC ATT TCT CAG CTC              831
Arg Val Lys Glu Ala Lys Gln Lys Ser Gln Glu Thr Ile Ser Gln Leu
                240                 245                 250

CAC TCC ACT GTC CAC CTG ATT GAA TTC GCC AGG AAG AAT ATG CAC AGT              879
His Ser Thr Val His Leu Ile Glu Phe Ala Arg Lys Asn Met His Ser
            255                 260                 265

GCC AAC CAG AAA ATT CAG GGT GCT CAG GAT AAG CTC TAT GTC TCG TGG              927
Ala Asn Gln Lys Ile Gln Gly Ala Gln Asp Lys Leu Tyr Val Ser Trp
                270                 275                 280

GTG GAG TGG AAG AGA AGC ATC GGC TAC GAC GAC ACC GAT GAG TCC CAC              975
Val Glu Trp Lys Arg Ser Ile Gly Tyr Asp Asp Thr Asp Glu Ser His
        285                 290                 295

TGT GTT GAG CAC ATC GAG TCA CGT ACT CTG GCT ATC GCC CGC AAC CTG             1023
Cys Val Glu His Ile Glu Ser Arg Thr Leu Ala Ile Ala Arg Asn Leu
300                 305                 310                 315

ACC CAG CAG CTC CAG ACT ACA TGC CAG ACT GTC CTG GTC AAC GCC CAA             1071
Thr Gln Gln Leu Gln Thr Thr Cys Gln Thr Val Leu Val Asn Ala Gln
                320                 325                 330

GGG TTA CCA CAG AAC ATT CAA GAT CAG GCC AAA CAC TTG GGG GTG ATG             1119
Gly Leu Pro Gln Asn Ile Gln Asp Gln Ala Lys His Leu Gly Val Met
                335                 340                 345

GCA GGC GAC ATC TAC TCC GTA TTC CGC AAT GCT GCC TCC TTT AAG GAA             1167
Ala Gly Asp Ile Tyr Ser Val Phe Arg Asn Ala Ala Ser Phe Lys Glu
                350                 355                 360

GTG TCC GAT GGC GTC CTC ACA TCT AGC AAG GGG CAG CTG CAG AAA ATG             1215
Val Ser Asp Gly Val Leu Thr Ser Ser Lys Gly Gln Leu Gln Lys Met
        365                 370                 375

AAG GAA TCC TTA GAT GAA GTT ATG GAT TAC TTT GTT AAC AAC ACG CCT             1263
Lys Glu Ser Leu Asp Glu Val Met Asp Tyr Phe Val Asn Asn Thr Pro
380                 385                 390                 395

CTC AAC TGG CTG GTA GGT CCC TTT TAT CCT CAG TCT ACC GAG GTG AAC             1311
Leu Asn Trp Leu Val Gly Pro Phe Tyr Pro Gln Ser Thr Glu Val Asn
                400                 405                 410

AAG GCC AGC CTG AAG GTC CAG CAG TCT GAG GTC AAA GCT CAG                     1353
Lys Ala Ser Leu Lys Val Gln Gln Ser Glu Val Lys Ala Gln
                415                 420                 425

TAAACCCCTC CTTGTCACCA GAGCATGATG TTGCTGGCCA GATGACCCCT TTTGCTGTAT           1413

TGAAATTAAC TTGGTAGATG GCTTTAGCTT AGAAAAGCAG CTTCTTAGAA CCAAGGGCCT           1473

CATTATGGTC ACTCACAGCT CAGTTATGGT CTTGCCCCAG CTGGCCCTGG CACAGGAGTT           1533

CTCTTACCTG GCTGGTGAGT GGCCTGTGTT AGTCTTGTGA GGACCTGGAG GAACCTAAAA           1593

GCTCAGATGC ACTTACAGTC TTGTCTGTGG CCTTTGTATT GTTATTGGCT GTAAACGTCT           1653

GTCTGGACCG AATAAAGATT CACGTGAAAA AA                                         1685
```

( 2 ) INFORMATION FOR SEQ ID NO:2:

( i ) SEQUENCE CHARACTERISTICS:
        ( A ) LENGTH: 425 amino acids ( B ) TYPE: amino acid
( D ) TOPOLOGY: linear ( i i ) MOLECULE TYPE: protein ( x i ) SEQUENCE DESCRIPTION: SEQ ID NO:2:

```
Met Ala Ala Ala Val Val Asp Pro Gln Gln Ser Val Val Met Arg Val
 1               5                  10                  15

Ala Asn Leu Pro Leu Val Ser Ser Thr Tyr Asp Leu Val Ser Ser Ala
                20                  25                  30

Tyr Val Ser Thr Lys Asp Gln Tyr Pro Tyr Leu Arg Ser Val Cys Glu
            35                  40                  45

Met Ala Glu Lys Gly Val Lys Thr Val Thr Ser Ala Ala Met Thr Ser
    50                  55                  60

Ala Leu Pro Ile Ile Gln Lys Leu Glu Pro Gln Ile Ala Val Ala Asn
65                  70                  75                  80

Thr Tyr Ala Cys Lys Gly Leu Asp Arg Met Glu Glu Arg Leu Pro Ile
                85                  90                  95

Leu Asn Gln Pro Thr Ser Glu Ile Val Ala Ser Ala Arg Gly Ala Val
                100                 105                 110

Thr Gly Ala Lys Asp Val Val Thr Thr Met Ala Gly Ala Lys Asp
            115                 120                 125

Ser Val Ala Ser Thr Val Ser Gly Val Val Asp Lys Thr Lys Gly Ala
    130                 135                 140

Val Thr Gly Ser Val Glu Arg Thr Lys Ser Val Val Asn Gly Ser Ile
145                 150                 155                 160

Asn Thr Val Leu Gly Met Val Gln Phe Met Asn Ser Gly Val Asp Asn
                165                 170                 175

Ala Ile Thr Lys Ser Glu Met Leu Val Asp Gln Tyr Phe Pro Leu Thr
            180                 185                 190

Gln Glu Glu Leu Glu Met Glu Ala Lys Lys Val Glu Gly Phe Asp Met
    195                 200                 205

Val Gln Lys Pro Ser Asn Tyr Glu Arg Leu Glu Ser Leu Ser Thr Lys
210                 215                 220

Leu Cys Ser Arg Ala Tyr His Gln Ala Leu Ser Arg Val Lys Glu Ala
225                 230                 235                 240

Lys Gln Lys Ser Gln Glu Thr Ile Ser Gln Leu His Ser Thr Val His
                245                 250                 255

Leu Ile Glu Phe Ala Arg Lys Asn Met His Ser Ala Asn Gln Lys Ile
            260                 265                 270

Gln Gly Ala Gln Asp Lys Leu Tyr Val Ser Trp Val Glu Trp Lys Arg
    275                 280                 285

Ser Ile Gly Tyr Asp Asp Thr Asp Glu Ser His Cys Val Glu His Ile
290                 295                 300

Glu Ser Arg Thr Leu Ala Ile Ala Arg Asn Leu Thr Gln Gln Leu Gln
305                 310                 315                 320

Thr Thr Cys Gln Thr Val Leu Val Asn Ala Gln Gly Leu Pro Gln Asn
                325                 330                 335

Ile Gln Asp Gln Ala Lys His Leu Gly Val Met Ala Gly Asp Ile Tyr
            340                 345                 350

Ser Val Phe Arg Asn Ala Ala Ser Phe Lys Glu Val Ser Asp Gly Val
    355                 360                 365

Leu Thr Ser Ser Lys Gly Gln Leu Gln Lys Met Lys Glu Ser Leu Asp
370                 375                 380

Glu Val Met Asp Tyr Phe Val Asn Asn Thr Pro Leu Asn Trp Leu Val
```

```
385                         390                         395                         400
Gly Pro Phe Tyr Pro Gln Ser Thr Glu Val Asn Lys Ala Ser Leu Lys
                405                         410                         415
Val Gln Gln Ser Glu Val Lys Ala Gln
            420                 425
```

( 2 ) INFORMATION FOR SEQ ID NO:3:

( i ) SEQUENCE CHARACTERISTICS:
      ( A ) LENGTH: 444 base pairs
      ( B ) TYPE: nucleic acid
      ( C ) STRANDEDNESS: single
      ( D ) TOPOLOGY: linear ( i i ) MOLECULE TYPE: cDNA ( i x ) FEATURE:
      ( A ) NAME/KEY: CDS
      ( B ) LOCATION: 1..444

( x i ) SEQUENCE DESCRIPTION: SEQ ID NO:3:

```
GAA TTC CGG GCA GAG AAC GGT GTG AAG ACC ATC ACC TCC GTG GCC ATG       48
Glu Phe Arg Ala Glu Asn Gly Val Lys Thr Ile Thr Ser Val Ala Met
 1               5                  10                  15

ACC AGT GCT CTG CCC ATC ATC CAG AAG CTA GAG CCG CAA ATT GCA GTT       96
Thr Ser Ala Leu Pro Ile Ile Gln Lys Leu Glu Pro Gln Ile Ala Val
             20                  25                  30

GCC AAT ACC TAT GCC TGT AAG GGG CTA GAC AGG ATT GAG GAG AGA CTG      144
Ala Asn Thr Tyr Ala Cys Lys Gly Leu Asp Arg Ile Glu Glu Arg Leu
         35                  40                  45

CCT ATT CTG AAT CAG CCA TCA ACT CAG ATT GTT GCC AAT GCC AAA GGC      192
Pro Ile Leu Asn Gln Pro Ser Thr Gln Ile Val Ala Asn Ala Lys Gly
     50                  55                  60

GCT GTG ACT GGG GCA AAA GAT GCT GTG ACG ACT ACT GTG ACT GGG GCC      240
Ala Val Thr Gly Ala Lys Asp Ala Val Thr Thr Thr Val Thr Gly Ala
 65                  70                  75                  80

AAG GAT TCT TTG GCC AGC ACG ATC ACA GGG GTG ATG GAC AAG ACC AAA      288
Lys Asp Ser Leu Ala Ser Thr Ile Thr Gly Val Met Asp Lys Thr Lys
                 85                  90                  95

GGG GCA GTG ACT GGC AGT GTG GAG AAG ACC AAG TCT GTG GTC AGT GGC      336
Gly Ala Val Thr Gly Ser Val Glu Lys Thr Lys Ser Val Val Ser Gly
            100                 105                 110

AGC ATT AAC ACA GTC TTG GGG AGT CGG ATG ATG CAG CTC GTG AGC AGT      384
Ser Ile Asn Thr Val Leu Gly Ser Arg Met Met Gln Leu Val Ser Ser
        115                 120                 125

GGC GTA GAA AAT GCA CTC ACC AAA TCA GAG CTG TTG GTA GAC CAG TAC      432
Gly Val Glu Asn Ala Leu Thr Lys Ser Glu Leu Leu Val Asp Gln Tyr
    130                 135                 140

CTC CCT CTC ACT                                                      444
Leu Pro Leu Thr
145
```

( 2 ) INFORMATION FOR SEQ ID NO:4:

( i ) SEQUENCE CHARACTERISTICS:
      ( A ) LENGTH: 148 amino acids
      ( B ) TYPE: amino acid
      ( D ) TOPOLOGY: linear ( i i ) MOLECULE TYPE: protein ( x i ) SEQUENCE DESCRIPTION: SEQ ID NO:4:

```
Glu Phe Arg Ala Glu Asn Gly Val Lys Thr Ile Thr Ser Val Ala Met
 1               5                  10                  15
```

| | | | | | | | | | | | | | | |
|---|---|---|---|---|---|---|---|---|---|---|---|---|---|---|
| Thr | Ser | Ala | Leu<br>20 | Pro | Ile | Ile | Gln | Lys<br>25 | Leu | Glu | Pro | Gln | Ile<br>30 | Ala | Val |
| Ala | Asn | Thr<br>35 | Tyr | Ala | Cys | Lys | Gly<br>40 | Leu | Asp | Arg | Ile | Glu<br>45 | Glu | Arg | Leu |
| Pro | Ile<br>50 | Leu | Asn | Gln | Pro | Ser<br>55 | Thr | Gln | Ile | Val | Ala<br>60 | Asn | Ala | Lys | Gly |
| Ala<br>65 | Val | Thr | Gly | Ala | Lys<br>70 | Asp | Ala | Val | Thr | Thr<br>75 | Thr | Val | Thr | Gly | Ala<br>80 |
| Lys | Asp | Ser | Leu | Ala<br>85 | Ser | Thr | Ile | Thr | Gly<br>90 | Val | Met | Asp | Lys | Thr<br>95 | Lys |
| Gly | Ala | Val | Thr<br>100 | Gly | Ser | Val | Glu | Lys<br>105 | Thr | Lys | Ser | Val | Val<br>110 | Ser | Gly |
| Ser | Ile | Asn<br>115 | Thr | Val | Leu | Gly | Ser<br>120 | Arg | Met | Met | Gln | Leu<br>125 | Val | Ser | Ser |
| Gly | Val<br>130 | Glu | Asn | Ala | Leu | Thr<br>135 | Lys | Ser | Glu | Leu | Leu<br>140 | Val | Asp | Gln | Tyr |
| Leu<br>145 | Pro | Leu | Thr | | | | | | | | | | | | |

What is claimed is:

1. An isolated and purified mammalian adipocyte p154 polypeptide, wherein said polypeptide is encoded by an mRNA molecule which is expressed in fat pad cells at a level of at least 10-fold higher than in brain, kidney or submaxillary gland cells, wherein the expression of said mRNA molecule is induced during differentiation of adipogenic cells.

2. A polypeptide according to claim 1 which is of human origin.

3. An isolated mammalian adipocyte p154 polypeptide of at least ten consecutive amino acids of the amino acid sequence 1–425 of SEQ ID NO: 2, which polypeptide is capable of serving as an antigen for the production of antibodies specific for an epitope of the entire protein of SEQ ID NO: 2.

4. An isolated mammalian adipocyte p154 polypeptide of at least 10 consecutive amino acids of the amino acid sequence 1–148 of SEQ ID NO:4, which polypeptide is capable of serving as an antigen for the production of antibodies specific for an epitope of the entire protein of SEQ ID NO:4.

5. An antibody specific for an epitope of a p154 polypeptide according to claim 3.

6. An antibody specific for an epitope of a p154 polypeptide according to claim 4.

7. An antibody according to claim 5 which is monoclonal.

8. A method for detecting the presence or measuring the quantity of a mammalian adipocyte p154 polypeptide in a biological sample, comprising:

(a) contacting said sample with an antibody according to claim 5; and (b) detecting the binding of said antibody to an antigen in said sample, or measuring the quantity of antibody bound, thereby detecting the presence or measuring the quantity of said polypeptide.

9. A method for determining the susceptibility of a subject to obesity which comprises removing a sample of a biological fluid or tissue from said subject and measuring therein the amount of a polypeptide as defined in claim 2, the amount of said polypeptide being proportional to said susceptibility.

10. A method for evaluating the efficacy of an anti-obesity drug, comprising, contacting said drug with an adipocyte in vitro and measuring the amount of a p154 polypeptide as defined in claim 1 produced by said adipocyte, the efficacy of said drug being proportional to the decrease in the production of said p154 polypeptide.

11. A method for detecting the presence or measuring the quantity of a mammalian adipocyte p154 polypeptide, in a biological sample, comprising:

(a) contacting said sample with an antibody according to claim 6; and (b) detecting the binding of said antibody to an antigen in said sample, or measuring the quantity of antibody bound, thereby detecting the presence or measuring the quantity of said polypeptide.

12. An antibody according to claim 6, which is monoclonal.

13. A polypeptide according to claim 1, having the amino acid sequence 1–425 of SEQ ID NO:2.

14. A polypeptide according to claim 1, having the amino acid sequence 1–148 of SEQ ID NO:4.

15. An antibody specific for an epitope of a p154 polypeptide according to claim 1.

16. An antibody specific for an epitope of a p154 polypeptide according to claim 13.

17. An antibody specific for an epitope of a p154 polypeptide according to claim 14.

18. An antibody according to claim 15 which is monoclonal.

19. An antibody according to claim 16, which is monoclonal.

20. An antibody according to claim 17, which is monoclonal.

21. A method for detecting the presence or measuring the quantity of a mammalian adipocyte p154 polypeptide in a biological sample, comprising:

(a) contacting said sample with an antibody according to claim 15; and (b) detecting the binding of said antibody to an antigen in said sample, or measuring the quantity of antibody bound, thereby detecting the presence or measuring the quantity of said polypeptide.

22. A method for detecting the presence or measuring the quantity of a mammalian adipocyte p154 polypeptide in a biological sample, comprising:
   (a) contacting said sample with an antibody according to claim 16; and
   (b) detecting the binding of said antibody to an antigen in said sample, or measuring the quantity of antibody bound, thereby detecting the presence or measuring the quantity of said polypeptide.

23. A method for detecting the presence or measuring the quantity of a mammalian adipocyte p154 polypeptide in a biological sample, comprising:
   (a) contacting said sample with an antibody according to claim 17; and
   (b) detecting the binding of said antibody to an antigen in said sample, or measuring the quantity of antibody bound, thereby detecting the presence or measuring the quantity of said polypeptide.

* * * * *